(12) United States Patent
Karavany et al.

(10) Patent No.: US 12,076,515 B2
(45) Date of Patent: *Sep. 3, 2024

(54) FLOW MODIFICATION IN BODY LUMENS

(71) Applicant: Nephronyx Ltd., Modiin (IL)

(72) Inventors: Sagy Karavany, Kibbutz Dvir (IL); Eyal Teichman, Hod-Hasharon (IL)

(73) Assignee: Nephronyx Ltd., Modiin (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/180,083

(22) Filed: Mar. 7, 2023

(65) Prior Publication Data

US 2023/0218872 A1 Jul. 13, 2023

Related U.S. Application Data

(63) Continuation of application No. 16/617,479, filed as application No. PCT/IB2018/053925 on May 31, 2018, now Pat. No. 11,607,532.

(Continued)

(51) Int. Cl.
*A61F 2/06* (2013.01)
*A61B 18/00* (2006.01)
(Continued)

(52) U.S. Cl.
CPC ............ *A61M 27/002* (2013.01); *A61F 2/06* (2013.01); *A61F 2/82* (2013.01); *A61M 25/0023* (2013.01);
(Continued)

(58) Field of Classification Search
CPC ............ A61M 27/002; A61M 25/0023; A61M 60/122; A61M 60/139; A61M 60/211;
(Continued)

(56) References Cited

U.S. PATENT DOCUMENTS 6,120,534 A * 9/2000 Ruiz .................. A61F 2/86
623/1.3
6,743,196 B2 6/2004 Barbut et al.
(Continued)

FOREIGN PATENT DOCUMENTS

WO WO-0197717 A1 12/2001
WO WO-2005048871 A2 6/2005
(Continued)

OTHER PUBLICATIONS

International Search Report & Written Opinion dated Feb. 13, 2020 in Int'l PCT Patent Appl. Serial No. PCT/IB2019/060142 (0510).
(Continued)

*Primary Examiner* — Kai H Weng
*Assistant Examiner* — Alessandro R Del Priore
(74) *Attorney, Agent, or Firm* — Greenberg Traurig, LLP; Christopher C. Bolten; Albert K. Heng

(57) ABSTRACT

The devices and methods described herein include an implantable body lumen fluid flow modulator including an upstream flow accelerator separated by a gap from a downstream flow decelerator. The gap is a pathway to entrain additional fluid from a branch lumen(s) into the fluid stream flowing from the upstream flow accelerator to the downstream flow decelerator.

19 Claims, 18 Drawing Sheets

Related U.S. Application Data

(60) Provisional application No. 62/537,067, filed on Jul. 26, 2017, provisional application No. 62/514,020, filed on Jun. 2, 2017.

(51) Int. Cl.
| | |
|---|---|
| *A61F 2/82* | (2013.01) |
| *A61M 25/00* | (2006.01) |
| *A61M 27/00* | (2006.01) |
| *A61M 60/122* | (2021.01) |

(52) U.S. Cl.
CPC .. *A61M 60/122* (2021.01); *A61B 2018/00511* (2013.01); *A61B 2018/00744* (2013.01); *A61F 2002/065* (2013.01); *A61F 2002/068* (2013.01); *A61F 2230/001* (2013.01); *A61F 2230/0067* (2013.01)

(58) Field of Classification Search
CPC .. A61M 60/33; A61F 2/06; A61F 2/82; A61F 2002/065; A61F 2002/068; A61F 2230/001; A61F 2230/0067; A61B 2018/00511; A61B 2018/00744; A61B 17/12109

See application file for complete search history.

(56) References Cited

U.S. PATENT DOCUMENTS

| | | | |
|---|---|---|---|
| 7,048,702 | B2 | 5/2006 | Hui |
| 7,384,389 | B2 | 6/2008 | Anzellini |
| 9,204,958 | B2 | 12/2015 | LaDuca et al. |
| 9,764,113 | B2 | 9/2017 | Tuval et al. |
| 10,195,406 | B2 | 2/2019 | Karavany et al. |
| 11,324,619 | B1 | 5/2022 | Yacoby et al. |
| 2001/0021872 | A1 | 9/2001 | Bailey et al. |
| 2004/0133260 | A1 | 7/2004 | Schwartz et al. |
| 2004/0143319 | A1 | 7/2004 | Schwartz et al. |
| 2004/0210236 | A1* | 10/2004 | Allers ............... A61M 1/3613 606/108 |
| 2005/0043790 | A1* | 2/2005 | Seguin ............... A61F 2/2403 623/2.18 |
| 2005/0055082 | A1* | 3/2005 | Ben Muvhar ......... A61F 2/91 623/1.15 |
| 2005/0222674 | A1 | 10/2005 | Paine |
| 2006/0106449 | A1* | 5/2006 | Ben Muvhar .... A61B 17/12172 623/1.15 |
| 2006/0149360 | A1* | 7/2006 | Schwammenthal .. A61F 2/2418 623/1.36 |
| 2007/0185565 | A1 | 8/2007 | Schwammenthal et al. |
| 2007/0293808 | A1 | 12/2007 | Williams et al. |
| 2009/0270965 | A1 | 10/2009 | Sinha et al. |
| 2010/0036307 | A1 | 2/2010 | Von Segesser |
| 2010/0063578 | A1 | 3/2010 | Ren et al. |
| 2010/0145433 | A1 | 6/2010 | Anukhin et al. |
| 2011/0282274 | A1* | 11/2011 | Fulton, III ....... A61B 17/12136 604/27 |
| 2011/0306916 | A1 | 12/2011 | Nitzan et al. |
| 2012/0095547 | A1 | 4/2012 | Chuter |
| 2012/0165928 | A1 | 6/2012 | Nitzan et al. |
| 2013/0338761 | A1* | 12/2013 | Plowiecki .............. A61F 2/954 623/1.35 |
| 2014/0350565 | A1* | 11/2014 | Yacoby ................ A61F 2/2418 606/108 |
| 2014/0350658 | A1* | 11/2014 | Benary .................. A61F 2/856 623/1.35 |
| 2015/0039020 | A1 | 2/2015 | Cragg et al. |
| 2015/0073470 | A1* | 3/2015 | Andersen ......... A61B 17/12109 606/200 |
| 2015/0164662 | A1* | 6/2015 | Tuval .................. A61F 2/2418 623/1.24 |
| 2015/0238315 | A1 | 8/2015 | Rabito et al. |
| 2015/0313603 | A1* | 11/2015 | Bödewadt ........ A61B 17/12109 606/191 |
| 2016/0128983 | A1 | 5/2016 | Djonov et al. |
| 2017/0112986 | A1 | 4/2017 | Heuring et al. |
| 2017/0128705 | A1 | 5/2017 | Forcucci et al. |
| 2017/0156845 | A1 | 6/2017 | Florescu |
| 2018/0014829 | A1 | 1/2018 | Tal et al. |
| 2018/0280667 | A1 | 10/2018 | Keren |
| 2019/0008628 | A1* | 1/2019 | Eigler ..................... A61F 2/91 |
| 2019/0069903 | A1 | 3/2019 | Deshmukh et al. |
| 2019/0167878 | A1 | 6/2019 | Rowe |
| 2019/0239998 | A1* | 8/2019 | Tuval ....................... A61F 2/06 |
| 2019/0298509 | A1 | 10/2019 | Sohn |
| 2021/0236727 | A1 | 8/2021 | Levin et al. |
| 2021/0244381 | A1 | 8/2021 | Sweeney et al. |
| 2022/0287831 | A1 | 9/2022 | Thornton |

FOREIGN PATENT DOCUMENTS

| | | | |
|---|---|---|---|
| WO | WO-2013183060 | A2 | 12/2013 |
| WO | WO-2014141284 | A2 | 9/2014 |
| WO | WO-2015177793 | A2 | 11/2015 |
| WO | WO-2016128983 | A1 | 8/2016 |
| WO | WO-2016185473 | A1 | 11/2016 |
| WO | WO-2018029688 | A1 | 2/2018 |
| WO | WO-2018061002 | A1 | 4/2018 |
| WO | WO-2018220589 | A1 | 12/2018 |
| WO | WO-2019097424 | A2 | 5/2019 |
| WO | WO-2019186538 | A1 | 10/2019 |
| WO | WO-2020109979 | A1 | 6/2020 |
| WO | WO-2021226014 | A2 | 11/2021 |
| WO | WO-2021240411 | A1 | 12/2021 |

OTHER PUBLICATIONS

International Search Report & Written Opinion dated Feb. 24, 2023 in Int'l PCT Patent Appl. Serial No. PCT/IB2022/06573 (0710).

International Search Report & Written Opinion dated Aug. 18, 2021 in Int'l PCT Patent Appl. Serial No. PCT/IB2021/054612 (0610).

Int'l Search Report & Written Opinion dated Sep. 17, 2018 in Int'l PCT Patent Appl. Serial No. PCT/IB2018/053925 (0410).

U.S. Appl. No. 15/995,101 / U.S. Pat. No. 10,195,406, May 31, 2018 / Feb. 5, 2019.

U.S. Appl. No. 16/617,479 / U.S. Pat. No. 11,607,523, Nov. 26, 2019 / Mar. 21, 2023.

U.S. Appl. No. 17/296,199, filed May 21, 2021.

U.S. Appl. No. 17/646,114 / U.S. Pat. No. 11,324,619, Dec. 27, 2021 / May 10, 2022.

U.S. Appl. No. 17/999,367, filed Nov. 18, 2022.

International Search Report & Written Opinion dated Mar. 18, 2024 in Int'l PCT Patent Appl. Serial No. PCT/IB2023/061404 (0810).

* cited by examiner

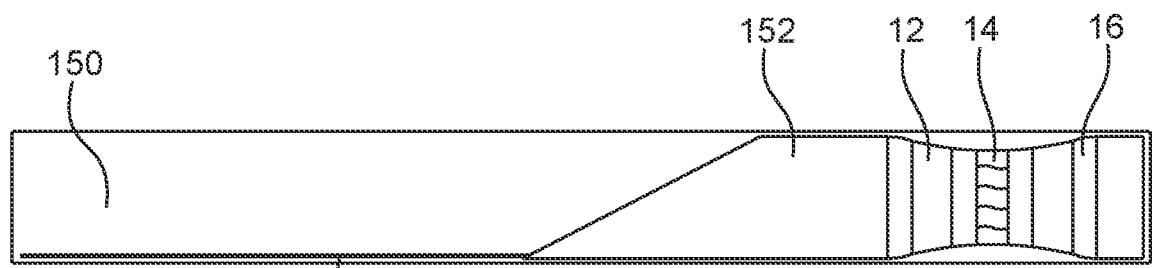
FIG. 30
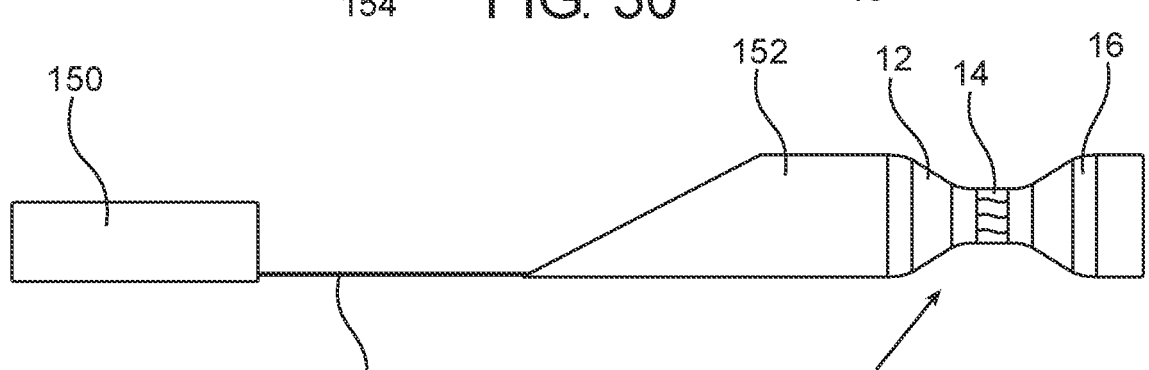
FIG. 31A
FIG. 31B
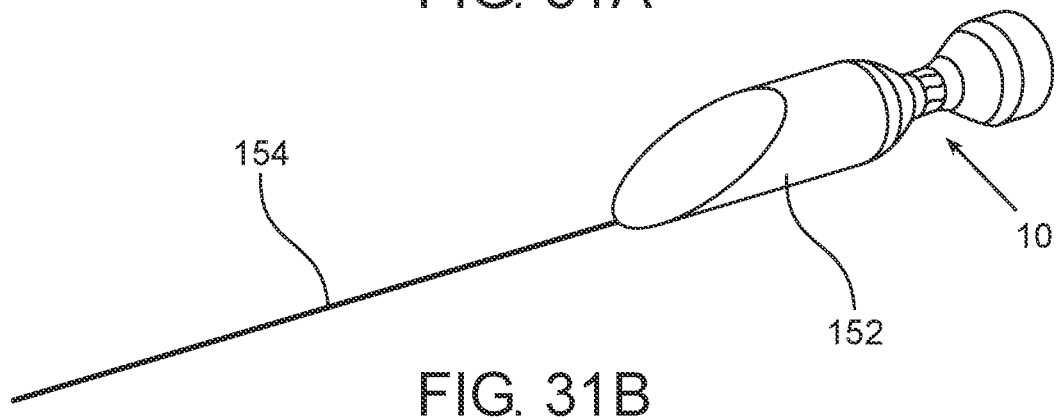
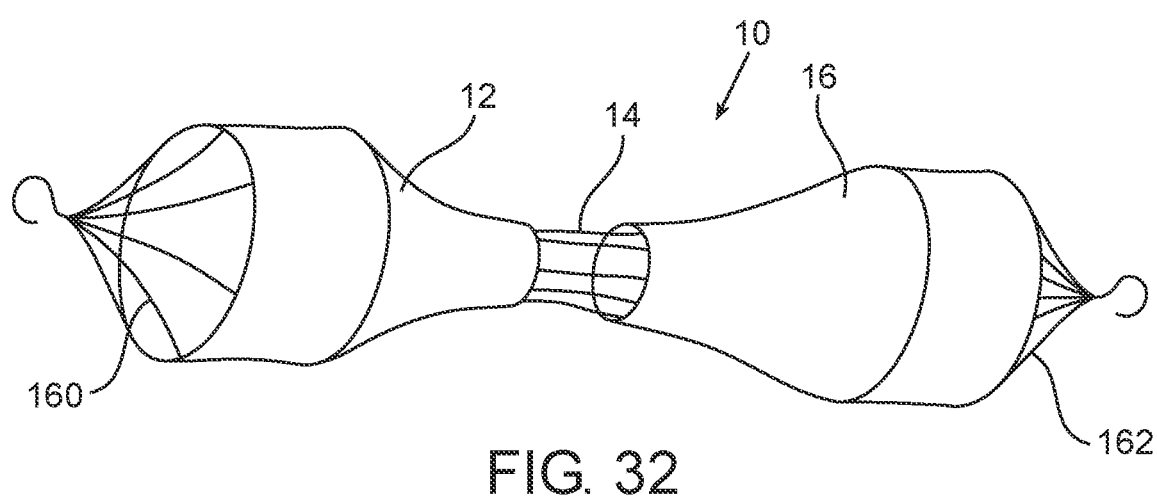
FIG. 32

FLOW MODIFICATION IN BODY LUMENS

CROSS-REFERENCE TO RELATED APPLICATIONS

This application is a continuation of U.S. patent application Ser. No. 16/617,479, filed Nov. 26, 2019, now U.S. Pat. No. 11,607,532, which is a national phase application under 35 U.S.C. § 371 of PCT/IB2018/053925, filed May 31, 2018, which claims the benefit of priority of U.S. Provisional Application Ser. No. 62/537,067, filed Jul. 26, 2017, and U.S. Provisional Application Ser. No. 62/514,020, filed Jun. 2, 2017, the entire contents of each of which are incorporated herein by reference. This application is also related to U.S. patent application Ser. No. 15/995,101, filed May 31, 2018, now U.S. Pat. No. 10,195,406, which claims the benefit of priority of U.S. Provisional Application Ser. No. 62/537,067, filed Jul. 26, 2017, and U.S. Provisional Application Ser. No. 62/514,020, filed Jun. 2, 2017, the entire contents of each of which are incorporated herein by reference.

FIELD OF THE INVENTION

The present invention relates generally to devices and methods for altering flow in body lumens, such as devices and methods for creating pressure differences and/or entrainment of fluid at lumens that branch off from other lumens for enhancing or modifying fluid flow to treat different disorders or diseases.

BACKGROUND OF THE INVENTION

Heart failure is the physiological state in which cardiac output is insufficient to meet the needs of the body and the lungs. Patients suffering from any of a number of forms of heart failure are prone to increased fluid in the body. Congestive heart failure (CHF) occurs when cardiac output is relatively low and the body becomes congested with fluid. There are many possible underlying causes of CHF, including myocardial infarction, coronary artery disease, valvular disease, and myocarditis. Chronic heart failure is associated with neurohormonal activation and alterations in autonomic control. Although these compensatory neurohormonal mechanisms provide valuable support for the heart under normal physiological circumstances, they also have a fundamental role in the development and subsequent progression of CHF. For example, one of the body's main compensatory mechanisms for reduced blood flow in CHF is to increase the amount of salt and water retained by the kidneys. Retaining salt and water, instead of excreting it into the urine, increases the volume of blood in the bloodstream and helps to maintain blood pressure. However, the larger volume of blood also stretches the heart muscle, enlarging the heart chambers, particularly the ventricles. At a certain amount of stretching, the heart's contractions become weakened, and the heart failure worsens. Another compensatory mechanism is vasoconstriction of the arterial system. This mechanism, like salt and water retention, raises the blood pressure to help maintain adequate perfusion.

Glomerular filtration rate (GFR), the rate at which the kidney filters blood, is commonly used to quantify kidney function and, consequently, the extent of kidney disease in a patient. Individuals with normal kidney function exhibit a GFR of at least 90 mL/min with no evidence of kidney damage. The progression of kidney disease is indicated by declining GFR, wherein a GFR below 15 mL/min generally indicates that the patient has end stage renal disease (ESRD), which is the complete failure of the kidney to remove wastes or concentrate urine.

Cardiovascular problems, such as but not limited to, inadequate blood flow or chronic hypertension, may lead to fluid retention in the kidneys, chronic kidney disease, lowered GFR, renal failure or even ESRD. For example, hypertension is considered the second most prevalent cause for kidney failure (after diabetes). It is been estimated that hypertension causes nephrotic damage and lowers GFR.

Therefore, it would be desirable to provide apparatus and methods to improve blood flow to prevent disease, improve body functionality, and/or treat conditions that would benefit from modified body fluid flow. For example, it would be desirable to treat heart failure, treat hypertension, prevent kidney disease, improve kidney functionality, and/or prevent blood clots from flowing through vasculature to sensitive portions of the body, such as the brain, in order to prevent strokes.

SUMMARY OF THE INVENTION

The present invention seeks to provide devices and methods for altering flow in body lumens, as is described more in detail hereinbelow. For example, devices and methods are provided for creating pressure differences and/or fluid entrainment at lumens that branch off from other lumens for enhancing or modifying fluid flow to treat different disorders or diseases.

The devices and methods of the present invention have many applications. For example, the device may be used to reduce pressure and improve flow, thereby improving flow in stenotic body lumens. It also may be used in the aortic arch to reduce peak systolic pressure in the brain or divert emboli to other portions of the body (e.g., the legs) and thereby reduce the risk of stroke. The device further may be installed in a bifurcation (e.g., in the brachiocephalic vessels) to reduce peak pressure gradients or to divert emboli with very little energy loss.

The devices and methods of the present invention have particular application in treating blood flow to and from the kidneys. In accordance with one embodiment, the device is configured to be installed near one of the renal arteries or in the inferior vena cava near the branch off to the renal veins or in one of the renal veins.

When installed in the inferior vena cava or in the renal vein, the device can create (due to the Bernoulli effect or other factors) a region in the inferior vena cava or in the renal vein which has increased blood velocity and reduced pressure. In this manner, blood may be drawn from the kidneys to the renal veins and then to the inferior vena cava, thereby improving kidney functionality and reducing necrotic damage to the kidneys.

When installed in or near the renal vein, the devices of the present invention may improve renal function by improving net filtration pressure, which is glomerular capillary blood pressure−(plasma-colloid osmotic pressure+Bowman's capsule hydrostatic pressure), e.g., 55 mm Hg−(30 mm Hg+15 mm Hg)=10 mm Hg. The devices and methods of the present invention thus provide an improvement over existing therapies, such as diuretics (although the invention can be used in addition to diuretics), angiotensin-converting enzyme inhibitors (ACEIs), and angiotensin receptor blockers (ARBs), which can have deleterious effects on kidney function. When used in conjunction with current modes of treatment such as diuretics, the devices and methods of the present invention are expected to improve the response for diuretics and reduce the dosage needed to obtain therapeutic benefit of such previously known therapies, without the disadvantages of these existing therapies.

The devices and methods of the present invention may be used to divert flow from the kidneys to the inferior vena cava with little energy loss. For example, with a small energy loss due to pressure drop and other fluid factors, a significantly greater increase in blood flow may be achieved. This diversion of flow from the kidneys with little energy loss to increase blood flow is expected to treat conditions such as heart failure and/or hypertension.

It is noted that there is a significant difference between use of an upstream nozzle with no downstream flow decelerator, such as a diffuser. If only an upstream nozzle is placed in the flow path, there is significant energy loss downstream of the nozzle due to the sudden expansion of flow. However, by using a downstream flow decelerator, such as a diffuser, the energy loss is significantly reduced. This leads to another advantage: since the energy loss is significantly reduced, the additional flow that flows into the gap is efficiently added to the flow from the upstream flow accelerator.

In addition, the present invention is expected to provide optimal structure for an upstream flow accelerator when used together with a downstream flow decelerator. For example, the distance between the outlet of the upstream flow accelerator and the inlet of the downstream flow decelerator should be less than a predetermined length to reduce pressure at the gap between the outlet and the inlet.

When installed in the renal artery, the device can reduce pressure applied to the kidneys. Without being limited by any theory, high blood pressure can cause damage to the blood vessels and filters in the kidney, making removal of waste from the body difficult. By reducing the pressure in the renal artery, the filtration rate improves. Although there may be a reduction in the perfusion pressure, the filtration rate will increase because the overall kidney function is more efficient.

It is noted that the fluid flow modulator of the present invention may modulate fluid flow without any input from an external energy source, such as a fan, motor, and the like and without any moving parts. The structure of the device of the invention transfers energy from one lumen flow to another different lumen flow with minimal flow energy losses.

In accordance with one aspect of the present invention, an implantable device is provided for altering fluid flow through a body lumen (e.g., the inferior vena cava) that is coupled to a branch lumen(s) (e.g., a renal vein(s)). The implantable device includes a flow modulator configured to be implanted within the body lumen. The flow modulator preferably has an upstream component separated by a gap from a downstream component. The flow modulator may be formed as a single unit (e.g., from a single frame) or multiple units. The upstream component has an inlet, an outlet, and a cross-sectional flow area that preferably converges from the inlet towards the outlet. The downstream component has an entry, an exit, and a cross-sectional flow area that preferably diverges from the entry towards the exit. The gap defines a pathway that communicates with the branch lumen, The flow modulator preferably accelerates a fluid stream passing through the upstream component towards the downstream component to generate a low pressure region in the vicinity of the gap and to entrain additional fluid into the fluid stream as the fluid stream passes into the entry of the downstream component.

The outlet of the upstream component is preferably spaced apart from the entry of the downstream component a suitable distance for increasing flow within the branch lumen(s) while minimizing pressure loss. For example, the distance from the outlet to the entry may be less than 15 mm.

In accordance with one aspect, the cross-sectional flow area at the outlet of the upstream component is less than the cross-sectional flow area at the entry of the downstream component. The outlet of the upstream component may be positioned downstream from where the branch lumen first intersects with the body lumen. The gap may begin downstream from where the branch lumen first intersects with the body lumen. The upstream component and the downstream component may share a common, collinear flow axis with the body lumen's flow axis. The outlet of the upstream component may be positioned downstream from the entry of the downstream component.

In one example, the upstream component is coupled to the downstream component via a fluid flow structure that defines the gap. The upstream component, the downstream component, and the fluid flow structure may be formed from a single frame. The fluid flow structure may extend outward from the upstream component and from the downstream component such that the fluid flow structure contacts an inner wall of the body lumen. A junction between the fluid flow structure and the upstream component and/or the downstream component may have a curved shape such as an S-curve shape.

In accordance with one aspect, the downstream component's length is greater than the upstream component's length. The upstream component's average angle of convergence may be greater than the downstream component's average angle of divergence. The upstream component may include a nozzle that accelerates the fluid stream passing through the upstream component and the downstream component may include a diffuser that decelerates the fluid stream having the entrained additional fluid passing through the downstream component.

The flow modulator may be formed from a metal frame. The metal frame may be coated with a biocompatible material at the upstream component and at the downstream component. In one example, an uncoated portion of the metal frame between the upstream and downstream components defines the gap that allows fluid from the branch lumen(s) to entrain with the fluid stream flowing through the flow modulator.

In accordance with another aspect, a method for altering fluid flow through a body lumen coupled to a branch lumen is provided. The method may include implanting a flow modulator within a body lumen, the flow modulator including an upstream component separated by a gap from a downstream component, the upstream component being implanted in a first body lumen portion and having an inlet, an outlet, and a cross-sectional flow area that converges from the inlet towards the outlet, the downstream component being implanted in a second body lumen portion and having an entry, an exit, and a cross-sectional flow area that diverges from the entry towards the exit. The gap may be positioned where the branch lumen intersects with the body lumen and the outlet may be positioned downstream from where the branch lumen first intersects with the body lumen. The method may include accelerating a fluid stream passing through the upstream component towards the downstream component to generate a low pressure region in the vicinity of the gap and to entrain additional fluid into the fluid stream as the fluid stream passes into the entry of the downstream component.

Implanting the flow modulator within the body lumen may include implanting the upstream component in an inferior vena cava such that the inlet is upstream from a branch off to a renal vein(s) and the downstream component in the inferior vena cava such that the exit is downstream from the branch off to the renal vein(s), wherein the gap is at the branch to the renal vein(s), thereby drawing blood from the renal vein(s) to the inferior vena cava and improving kidney functionality. Drawing the blood from the renal vein(s) to the inferior vena cava to improve kidney functionality may further reduce excess fluid to treat heart failure.

The flow modulator may modulate fluid flow without any input from an external energy source. The flow modulator may modulate fluid flow without any moving parts.

There is thus provided in accordance with an embodiment of the present invention a system including a body-lumen fluid flow modulator including an upstream flow accelerator separated by a gap from a downstream flow decelerator, wherein the gap is a pathway to entrain additional fluid with fluid flowing from the upstream flow accelerator, to the downstream flow decelerator.

The gap may be located in a fluid flow structure that defines boundaries for the pathway to entrain the additional fluid to flow to the downstream flow decelerator. The upstream flow accelerator may have a flow cross-section that converges in a downstream direction. The downstream flow decelerator may have a flow cross-section that diverges in a downstream direction. The fluid flow structure may include one or more conduits that are not collinear with a direction of flow from the upstream flow accelerator to the downstream flow decelerator. The upstream flow accelerator and the downstream flow decelerator may share a common, collinear flow axis. The fluid flow structure may or may not connect the upstream flow accelerator to the downstream flow decelerator. The fluid flow structure may diverge outwards in a direction away from a central axis of the fluid flow structure. A junction between the fluid flow structure and at least one of the upstream flow accelerator and the downstream flow decelerator may be curved.

There is provided in accordance with an embodiment of the present invention a method for altering fluid flow through a body lumen including installing a fluid flow modulator in a body, the fluid flow modulator including an upstream flow accelerator separated by a gap from a downstream flow decelerator, the upstream flow accelerator being installed in a first body lumen portion, the downstream flow decelerator being installed in a second body lumen portion and the gap being positioned at a branch lumen tilted with respect to the first and second body lumen portions, wherein when fluid flows from the upstream flow accelerator to the downstream flow decelerator, additional fluid is entrained into the gap and is added to the fluid flowing from the upstream flow accelerator to the downstream flow decelerator.

In one method, the fluid flow modulator is installed near renal arteries to improve renal function by reducing renal perfusion pressure.

In one method, the fluid flow modulator is installed near a bifurcation to divert emboli from the bifurcation.

In one method, the fluid flow modulator is installed in an aortic arch to reduce peak systolic pressure.

BRIEF DESCRIPTION OF THE DRAWINGS

The present invention will be understood and appreciated more fully from the following detailed description taken in conjunction with the drawings in which:

FIGS. 29A and 29B are views of an upstream flow accelerator or a downstream flow decelerator, whose shape is changeable in accordance with another non-limiting embodiment of the present invention, wherein FIG. 29B is a sectional view taken along lines B-B in FIG. 29A;

FIGS. 30-34 are schematic views of fluid flow modulators, in accordance with non-limiting embodiments of the present invention, shown in delivery and retrieval-type configurations.

DETAILED DESCRIPTION OF EMBODIMENTS

Provided herein are devices and methods for altering flow in body lumens. For example, the devices and methods may be provided for creating pressure differences and/or fluid entrainment at lumens that branch off from other lumens for enhancing or modifying fluid flow to treat different disorders or diseases.

Figure 1:
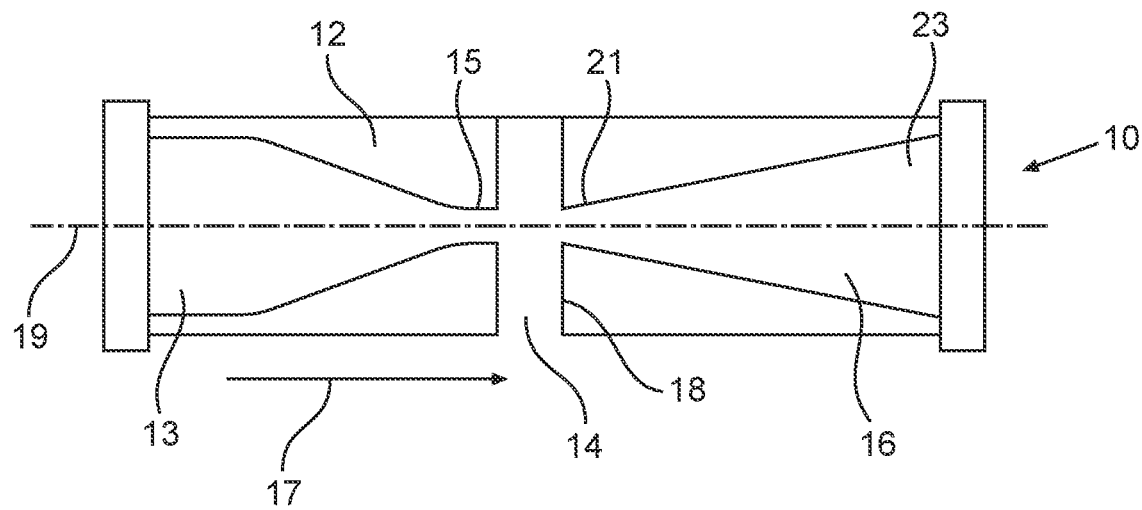
FIG. 1 is a schematic view of a fluid flow modulator, constructed and operative in accordance with a non-limiting embodiment of the present invention.

Reference is now made to FIG. 1, which illustrates flow modulator 10, constructed and operative in accordance with a non-limiting embodiment of the present invention.

Flow modulator 10 includes upstream component 12 separated by gap 14 from downstream component 16. Gap 14 is a pathway to divert or entrain additional fluid into a stream of fluid flowing from upstream component 12 to downstream component 14. As will be explained below, upstream component 12 and downstream component 16 create a lower pressure region in the vicinity of gap 14, which preferably entrains fluid into the stream of fluid flowing across gap 14. Fluid entrainment is fluid transport by shear-induced turbulent flux. In accordance with the principles of the invention, such entrainment may help transport blood or other body fluids to or from a region so as to promote better functionality of an organ (e.g., from the renal vein(s) to the inferior vena cava to promote better functionality of the kidney(s), thereby treating disorders and/or diseases such as heart failure).

Upstream component 12 has inlet 13 and outlet 15 and preferably has a cross-sectional flow area that converges in a downstream direction (indicated by arrow 17) along part or all of the length of upstream component 12, such as but not limited to, a nozzle. In this manner, upstream component 12 acts to accelerate flow of fluid through upstream component 12. Downstream component 16 has entry 21 and exit 23 and preferably has a cross-sectional flow area that diverges in a downstream direction along part or all of the length of downstream component 16, such as but not limited to, a diffuser. In this manner, downstream component 16 acts to decelerate flow of fluid through downstream component 16. The distance between outlet 15 and entry 21 is selected to generate a low pressure region in the vicinity of gap 14 while minimizing pressure loss and reducing resistance to fluid flow at the branch lumen(s), e.g., renal flow. For example, as explained in the data below, a distance too great will create a significant pressure loss that actually sends flow in the wrong direction in a branched lumen. Applicant has discovered that using a maximum distance between outlet 15 and entry 21 (e.g., less than 25 mm and more preferably less than 15 mm when used at the renal veins) will improve flow rates in the branched vessel(s) with relatively low pressure loss. Gap 14 also permits flow modulator 10 to entrain additional fluid into the fluid stream as the fluid stream passes into entry 21 of downstream component 16.

PCT Patent Applications WO 2016/128983 and WO 2018/029688, as well as U.S. Provisional Application Nos. 62/586,258 and 62/630,406, describe several converging and diverging structures which may be utilized for creating flow modulator 10 in accordance with the principles described herein, and the disclosures of each of which are incorporated herein by reference in their entireties. Other non-limiting converging and diverging structures are shown in FIGS. 2-34. The invention may be carried out with different kinds of converging and diverging structures, such as but not limited to, Stratford ramp nozzles (e.g., in which flow through the nozzle is on the verge of separation, which gives the diffuser the best length to efficiency ratio), de Laval nozzles (e.g., asymmetric hourglass shape), variable cross-sectional area nozzles and venturis, ramped nozzles and venturis, and many others. The central axis of the diverging portion may be in-line with or offset from the central axis of the converging portion.

Gap 14 may be located in fluid flow structure 18 which defines boundaries for the pathway to divert or entrain the additional fluid to flow to downstream component 16. Fluid flow structure 18 may include one or more conduits that are not collinear with a direction of flow (indicated by arrow 17) from upstream component 12 to downstream component 16. For example, the conduits of fluid flow structure 18 may be perpendicular to direction of flow or may be tilted at an angle, e.g., 30° angle, 45° angle or any other suitable configuration.

In the embodiment of FIG. 1, upstream component 12 and downstream component 16 share a common, collinear flow axis 19. However, the invention is not limited to this construction and upstream component 12 may be tilted with respect to downstream component 16. Upstream component 12 and downstream component 16 may lie along a continuous curved path.

Fluid flow structure 18 may or may not connect upstream component 12 to downstream component 16. For example, if fluid flow structure 18 employs conduits, then fluid flow structure 18 preferably connects upstream component 12 to downstream component 16. However, fluid flow structure 18 as shown in FIG. 1 may not be conduits, but instead two walls that are not connected to each other. In such an example, fluid flow structure 18 does not connect upstream component 12 to downstream component 16.

Upstream component 12, downstream component 16, and fluid flow structure 18 may be constructed as grafts, stents (coated or uncoated), stent grafts (coated or uncoated), catheters and the like, with known medically safe materials, such as stainless steel or nitinol. The outer contours of any of upstream component 12, downstream component 16, and fluid flow structure 18 may be sealed against the inner walls of the body lumen (such as by being expanded thereagainst), or alternatively may not be sealed, depending on the particular application.

Flow modulator 10 is sized and shaped to be implanted in a body lumen. Flow modulator 10 may be compressible for delivery (e.g., percutaneous delivery within a delivery sheath) and expandable upon deployment (e.g., self-expanding upon exposure from the end of the delivery sheath or balloon expandable). Flow modulator 10 may be inserted into the body lumen in an antegrade or retrograde manner and may be removed antegrade or retrograde. Flow modulator may be used as an acute device to be removed after few hours/days or a chronic permanent device or a device that can be retrieved after long-term implantation. When used as an acute device, flow modulator 10 may remain coupled to a delivery/retrieval device, e.g., sheath and/or wire/shaft, throughout the short-term implantation for ease of device delivery and retrieval. Flow modulator 10 may be compressible within a body lumen to allow washing of any stagnant flow zones created adjacent to flow modulator 10. For example, flow modulator 10 may be partially or fully reduced in diameter within the body lumen to allow blood flow through a stagnant flow zone. Preferably, upon expansion, flow modulator 10 is sized to contact the inner wall of the body lumen to anchor flow modulator 10 in place. Flow modulator 10 preferably is formed from one or more frames and may be coated with one or more biocompatible materials. For example, the frame(s) may be formed of a metal (e.g., shape memory metal) or alloy or a combination thereof (e.g., a stent made of stainless steel or nitinol or cobalt chromium). For some applications, the frame(s) may be formed in the manner of a braided stent. In the case of more than one frame, the frames may be joined together by a suitable technique such as welding. For example, upstream component 12 and downstream component 16 may be formed from a common frame or two frames that may be joined prior to implantation. Flow modulator 10 may be at least partially coated with a biocompatible, covering material (although they may be used as bare metal, uncoated stents as well). The biocompatible material may be a fabric and/or polymer such as expanded polytetrafluoroethylene (ePTFE), woven, knitted, and/or braided polyester, polyurethane, DACRON (polyethylene terephthalate), silicone, polycarbonate urethane, or pericardial tissue from an equine, bovine, or porcine source. The biocompatible coating may impede or block fluid flow where applied to the frame. The order of the joining and coating processes may be joining before coating or coating before joining. The biocompatible material may be coupled to the frame(s) via stitching, spray coating, encapsulation, electrospinning, dip molding, and/or a different technique.

In a preferred embodiment, biocompatible material is fluid impermeable. However, for some applications, the surfaces need not be impermeable, but have a permeability that is sufficiently low as to substantially prevent any blood from flowing through the longitudinal portion of the body lumen, via any flow path other than through the flow channel defined by the inner surfaces of flow modulator 10. For some applications, each of the surfaces has permeability per unit length of less than 0.25 micrometers (i.e., between 0 and 0.25 micrometers), where the permeability per unit length is defined based upon the following equation, which is based upon Darcy's Law: k/Δx=Vμ/Δp, where k is permeability, Δx is length (in meters), V is average velocity (in meters per second), u is fluid viscosity (measured in Pascal-seconds), and ΔP is the pressure differential measured in Pascals).

Although the invention is not bound by any theory, a simplified engineering explanation is now provided to help understand how upstream component 12 and downstream component 16 operate to create reduced pressure at gap 14.

The Bernoulli equation governs the relationship between fluid velocity and pressure (neglecting the height difference):

$$P_1 + \frac{1}{2} \cdot \rho \cdot V_1^2 = P_2 + \frac{1}{2} \cdot \rho \cdot V_2^2 + E_{loss}$$

P=pressure
ρ=density
V=velocity
1=conditions at the inlet (upstream component 12)
2=conditions at gap 14
Mass conservation (same flow rate):

$$V_1 \cdot A_1 = V_2 \cdot A_2$$

A=Flow cross section
$E_{loss}$=Energy loss

For example, if flow modulator 10 is installed near the kidneys with upstream component 12 in the inferior vena cava, then $V_1$ and $A_1$ are the renal velocity and flow area, respectively, at the inferior vena cava.

The flow velocity at the gap ($V_2$) is designed to achieve the desired pressure reduction. For example, without limitation, with a 0.5 meter per second velocity and 3 times area ratio, a suction of ~6-8 mmHg can be achieved. In the case of installation near the kidney, this can improve renal function by improving renal perfusion pressure.

In another example, flow modulator 10 can be installed near a bifurcation to divert emboli from the bifurcation. In another example, flow modulator 10 can be installed in the aortic arch to reduce peak systolic pressure.

Figure 2:
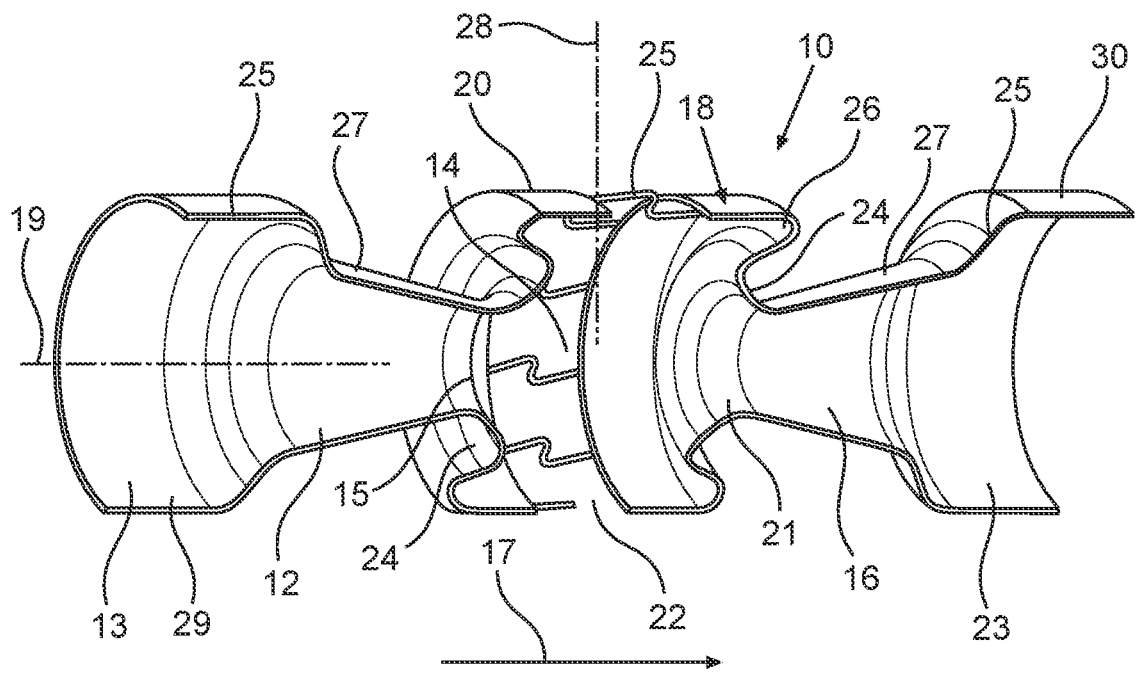
FIG. 2 is a side-sectional view of a fluid flow modulator, constructed and operative in accordance with another non-limiting embodiment of the present invention.

Reference is now made to FIG. 2, which illustrates another version of flow modulator 10, with like elements being designated by like numerals. In this version, fluid flow structure 18 includes central portion 20, which may be cylindrical, that connects upstream component 12 to downstream component 16. Fluid flow structure 18 extends outward from outlet 15 of upstream component 12 and from entry 21 of downstream component 16 such that fluid flow structure 18 is sized to contact an inner wall of the body lumen. Central portion 20 may be formed with one or more apertures 22 to define gap 14 for fluidly communicating with branch lumens such that additional fluid from the branch lumen or lumens flows into gap 14 and is added to the fluid flowing from upstream component 12 to downstream component 16.

It is noted that junction 24 between fluid flow structure 18 and upstream component 12 and/or downstream component 16 is curved. This may help streamline the flow, and prevent creation of local turbulences or eddy currents that may adversely affect the pressure or flow characteristics. It is also noted that fluid flow structure 18 may diverge outwards (at numeral 26) in a direction away from central axis 28 of fluid flow structure 18. This diversion may be used to create different flow affects, depending on the application. The diversion also enables moving upstream component 12 and downstream component 16 closer to each other. For example, junction 24 between fluid flow structure 18 and upstream and downstream components 12 and 16 may be S-shaped to move outlet 15 closer to entry 21 to minimize the distance between those parts of fluid modulator 10.

As best shown in FIG. 2, fluid modulator 10 is formed from frame 25 and coated with biocompatible material 27. The potential materials for frame 25 and biocompatible material 27 are described above. In FIG. 2, fluid modulator 10 is formed of one frame that defines upstream component 12, gap 14, and downstream component 16. Upstream component 12 is coated with biocompatible material 27 to define the fluid flow channel through upstream component 12 such that fluid flowing through a body lumen enters inlet 13, accelerates through the converging portion of upstream component 12, and exits out outlet 15 into the portion of fluid modulator 10 having gap 14. At gap 14, there is a low pressure region formed by the shapes of upstream component 12 and downstream component 16. Also, additional fluid from the branch lumen(s) at gap 14 is entrained into the fluid stream passing from outlet 15 to entry 21. Downstream component 16 also is coated with biocompatible material 27 to define the fluid flow channel through downstream component 16 such that the fluid stream from outlet 12 together with the additional fluid passing through gap 14 enter entry 21, decelerate through the diverging portion of downstream component 16, and exit out exit 23 back into the body lumen. In this example, gap 14 is created by an uncoated portion of frame 25.

Upstream component 12 may have fixation area 29 sized for anchoring upstream component 12 within the body lumen. Fixation area 29 is sized to contact the inner wall of the body lumen and preferably has a diameter the size of, or slightly larger than, the diameter of the body lumen. Fixation area 29 may have a constant diameter for a length suitable for anchoring upstream component 12 in the body lumen. Similarly, downstream component 16 may have fixation area 30 sized for anchoring downstream component 16 within another portion of the body lumen. Fixation area 30 is sized to contact the inner wall of the other portion of the body lumen and preferably has a diameter the size of, or slightly larger than, the diameter of that portion of the body lumen. Fixation area 30 may have a constant diameter for a length suitable for anchoring downstream component 16 in the body lumen. Preferably fixation areas 29 and 30 are configured to seal fluid modulator 10 within the body lumen so that fluid only flows into the fluid channels created by fluid modulator 10 and does not flow around fixation area 29 or fixation area 30. In FIG. 2, fluid flow structure 18 has the same diameter as fixation areas 29 and 30, which may enhance anchoring immediately proximal and distal to the branch lumen(s) while positioning gap 14 at the intersection between the body lumen and the branch lumen(s). In this manner, fluid flow structure 18 forms one or more additional fixation areas (illustratively, two additional fixation areas) between fixation areas 29 and 30. As shown, the portions of fluid flow structure 18 coated with biocompatible material 27 (on opposing sides of uncoated frame 25 that defines gap 14) act as fixation/scaling areas. Fluid flowing in the body lumen may be trapped between the outer surface of upstream component 12 and the body lumen wall between fixation area 29 and the upstream portion of fluid flow structure 18. In addition, or alternatively, fluid flowing in the body lumen may be trapped between the outer surface of downstream component 16 and the body lumen wall between fixation area 30 and the downstream portion of fluid flow structure 18.

Figure 3A:
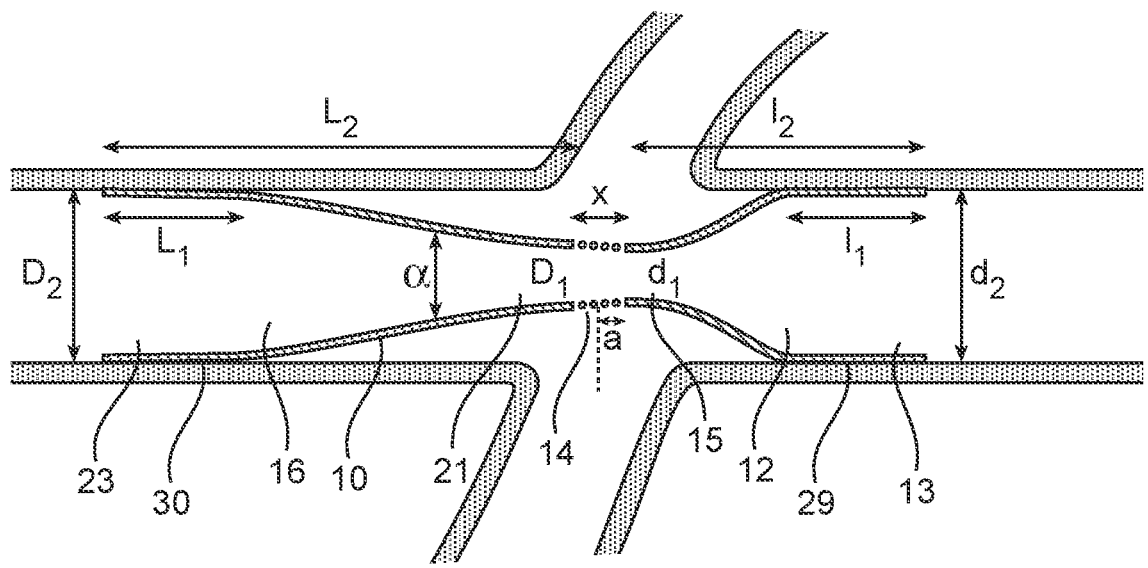
FIGS. 3A-19 are schematic views of different fluid flow modulators of the invention, some of which are shown installed in various body lumens, in accordance with non-limiting embodiments of the present invention.

Referring now to FIG. 3A, an exemplary flow modulator is shown with symbols depicting dimensions of flow modulator 10 in accordance with a preferred embodiment. The dimensions provided with respect to FIG. 3 are for an embodiment where flow modulator 10 is configured for implantation in the inferior vena cava such that inlet 13 of upstream component 12 is upstream from a branch off to a renal vein(s) and downstream component 16 is in the inferior vena cava such that exit 23 is downstream from the branch off to the renal vein(s) and gap 14 is at the branch to the renal vein(s). d1 is the diameter of outlet 15 of upstream component 12. d1 is selected to create a jet velocity for a given device resistance. In the example of chronic cases, d1 may be in a range from 4-8 mm. In acute cases, d1 preferably is in a range from 3-7 mm. d2 is the diameter of inlet 13 in the deployed, expanded state and may be in a range from 12-40 mm. l1 is the length of fixation area 29 and may be in a range from 5-30 mm. l2 is the overall length of upstream component 12 and may be in a range from 15-60 mm. x is the distance from outlet 15 of upstream component 12 to entry 21 of downstream component. For x, a minimum distance from outlet 15 to entry 21 will provide better performance for downstream component 16, but the renal flow will be lower because there is a greater resistance to flow from the renal vein(s) to downstream component 16. Thus, distance x preferably is selected (e.g., in a range from −5-25 mm) to provide improved renal flow rate with minimal pressure loss.

As illustrated below, distance x may be negative as outlet 15 of upstream component 12 may be positioned downstream from entry 21 of downstream component 16. a is the distance from outlet 15 of upstream component 12 to the center line of the branched lumen, e.g., the right renal vein, and may be in a range from −25-25 mm. L1 is the length of fixation area 30 and may be in a range from 5-30 mm. L2 is the overall length of downstream component 16. L2 is preferably greater than l2 because a diverging shape creates a much higher pressure loss than a converging shape. The ratio of L2:l2 may be from 1:1 to 3:1. D1 is the diameter at entry 21 of downstream component 16 and is preferably larger than d1. Thus, the cross-sectional flow area at outlet 15 of upstream component 12 is less than the cross-sectional flow area at entry 21 of downstream component 16. D1 is selected to receive all the fluid jetted from outlet 15. The ratio of D1:d1 may be from 1:1 to 2:1. In addition, D1 should be greater for larger distances x to ensure receipt of the fluid jetted from upstream component 12. D2 is the diameter of exit 23 in the deployed, expanded state and may be in a range from 12-40 mm. α is the average angle of divergence in downstream component 16 and may be in a range from 5-30 degrees. Preferably, the angle of divergence in downstream component 16 is less than the angle of convergence in upstream component 12, as illustrated. Such structure is expected to prevent pressure loss. In addition, downstream component 16 should have slow change in area adjacent to entry 21 (closer to the renal vein)—any additional pressure loss will reduce the inferior vena cava flow rate and thus will reduce the effectiveness of the device. The angle of divergence in downstream component 16 may be constant or may change along the length of downstream component 16. When the angle of divergence changes along the length (as shown in FIG. 2, for example) the angle of divergence is preferably smallest (e.g., in a range from 5-30 degrees) adjacent to entry 21. A slow change in the cross-sectional flow area adjacent to entry 21 is preferable because the fluid velocity decreases as the cross-sectional flow area increases, hence the pressure loss. Accordingly, the angle of divergence is smallest at entry 21 where the fluid flow is at maximum velocity within downstream component 16.

Fluid modulator 10 of FIG. 3A may be formed from one frame that defines upstream component 12, gap 14, and downstream component 16. In this example, upstream component 12 and downstream component 16 are each coated with a biocompatible material while gap 14 is created by an uncoated portion of the frame.

Figure 3B:
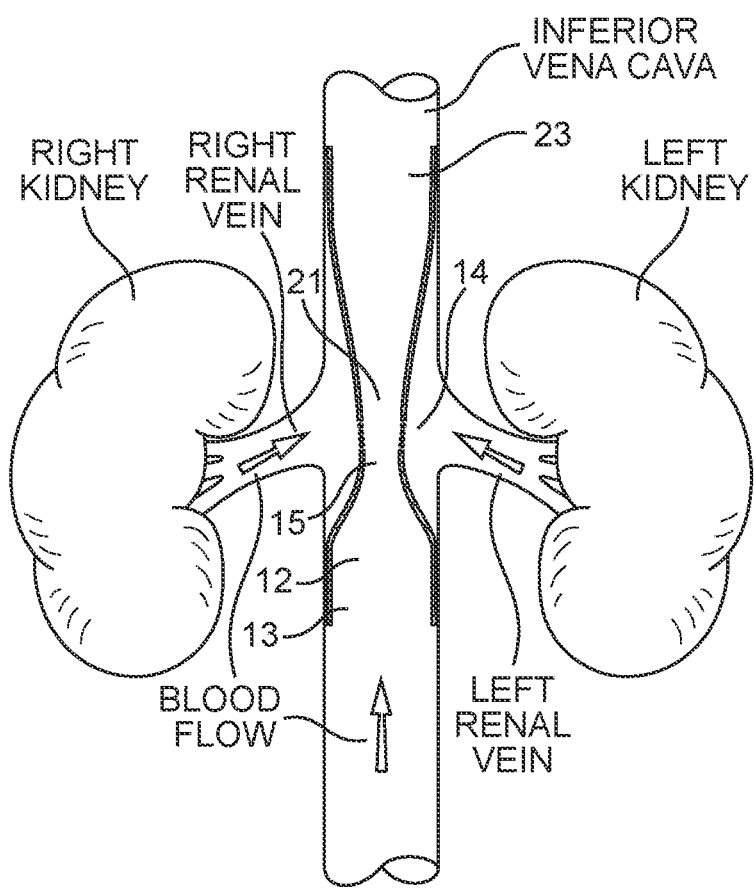

FIG. 3B shows flow modulator 10 of FIG. 3A implanted in the inferior vena cava at the renal veins. Upstream component 12 is in the inferior vena cava such that inlet 13 is upstream from a branch off to the left and right renal veins and downstream component 16 is in the inferior vena cava such that exit 23 is downstream from the branch off to the renal veins. While the right and left renal veins are usually at different heights along the inferior vena cava, gap 14 is generally positioned in the vicinity of the branches to the renal veins (or other branch lumens when used for other indications). For example, gap 14 may begin downstream from where the renal veins first intersect with the inferior vena cava, as illustrated. In addition, gap 14 may be entirely disposed within the intersection between the renal veins and the inferior vena cava, as illustrated. Outlet 15 of upstream component 12 may be positioned downstream from where the renal veins first intersect with the inferior vena cava, as shown. Accordingly, blood only enters fluid modulator 10 at inlet 13 and gap 14, which is downstream from where the branch lumen first intersects the main lumen. Entry 21 of downstream component 16 may be positioned upstream from where the intersection of the renal veins and the inferior vena cava ends, as shown. Flow modulator 10 creates reduced pressure at gap 14 and increases blood flow velocity to gap 14. Entrainment may also help transport blood to gap 14 from the kidneys. In this manner, the invention may draw blood from the kidneys to the renal veins and then to the inferior vena cava, thereby improving kidney functionality, reducing necrotic damage to the kidneys, and/or treating heart failure.

Reference is now made to FIGS. 4-29B, which illustrate different flow modulators of the invention, in accordance with non-limiting embodiments of the present invention. Once again, like elements are designated by like numerals.

Figure 4:
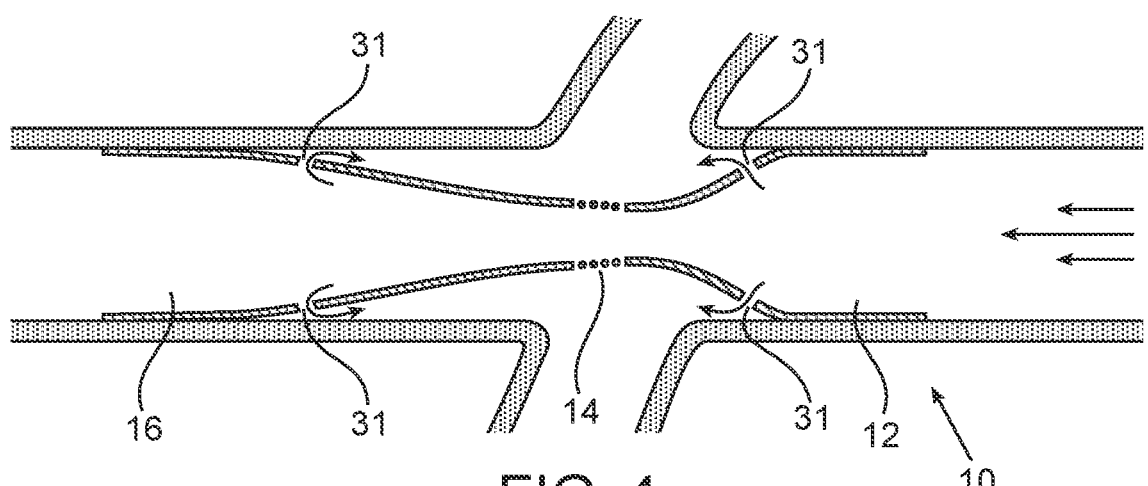

In FIG. 4, flow modulator 10 is constructed similarly to fluid modulator of FIG. 3A although flow modulator 10 of FIG. 4 includes one or more openings 31 to prevent stagnant flow zones. Fluid entering fluid modulator 10 flows out of openings 31 and into the body lumen. Openings 31 act as flashing flow channels for fluid and may encompass the entire circumference of fluid modulator 10 or be ports. Upstream component 12 or downstream component 16 or both (as illustrated) may include one or more openings 31. As shown, openings 31 may be on the converging portion of upstream component 12 and/or on the diverging portion of downstream component 16. When openings 31 are utilized, they are preferably at least on downstream component 16 as downstream component 16 is preferably longer than upstream component 12, making downstream component 16 more prone to a larger stagnant flow zone.

Figure 5:
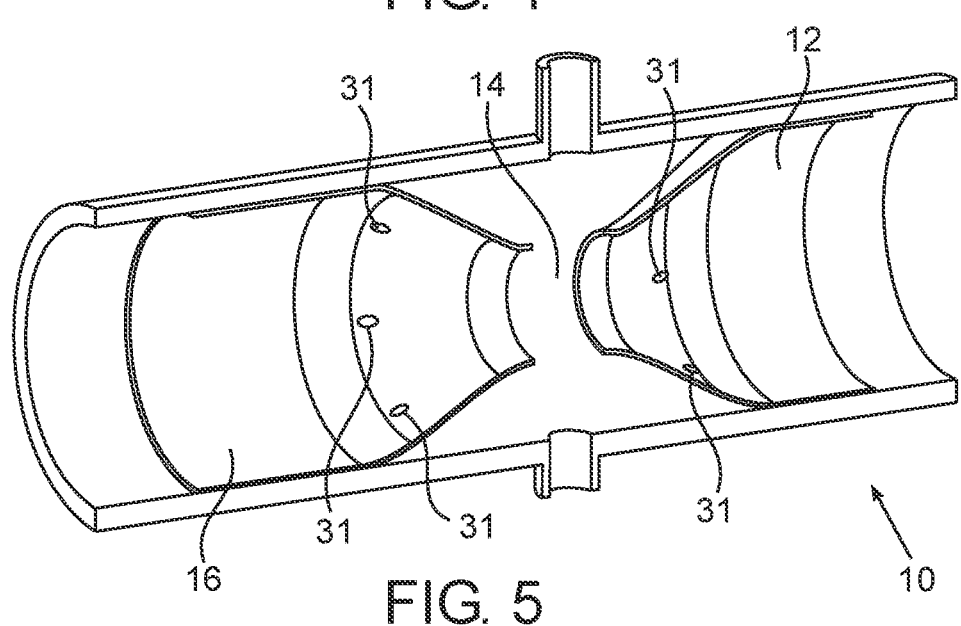

FIG. 5 is a cross-sectional view of fluid modulator 10 with a plurality of openings 31 that act as flashing flow channels.

Figure 6:
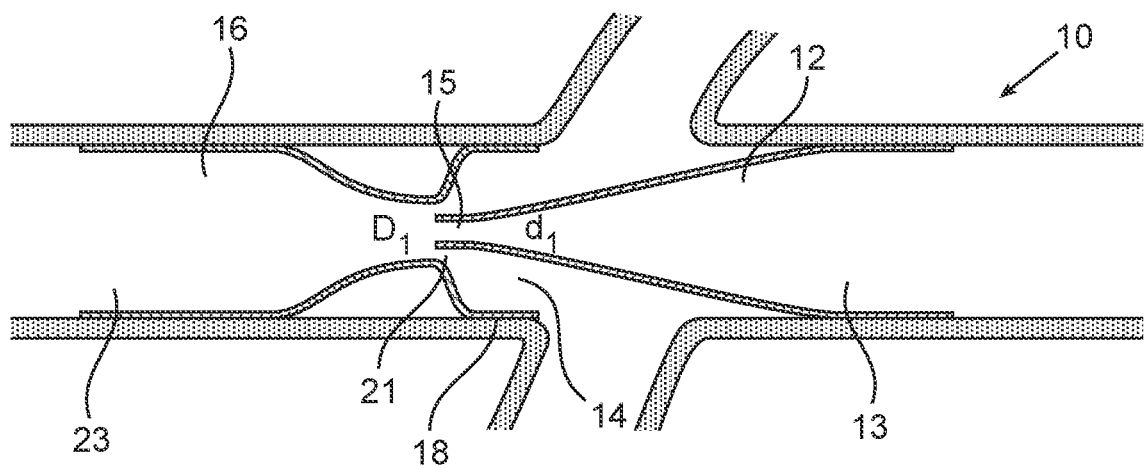

FIG. 6 illustrates fluid modulator 10 where outlet 15 of upstream component 12 is positioned downstream from entry 21 of downstream component 16. In this example, distance x is negative and D1 is larger than d1, e.g., at least 1 mm larger. As shown, outlet 15 and entry 21 may both be positioned downstream past the intersection of the branch lumen(s) and the body lumen.

Figure 7:
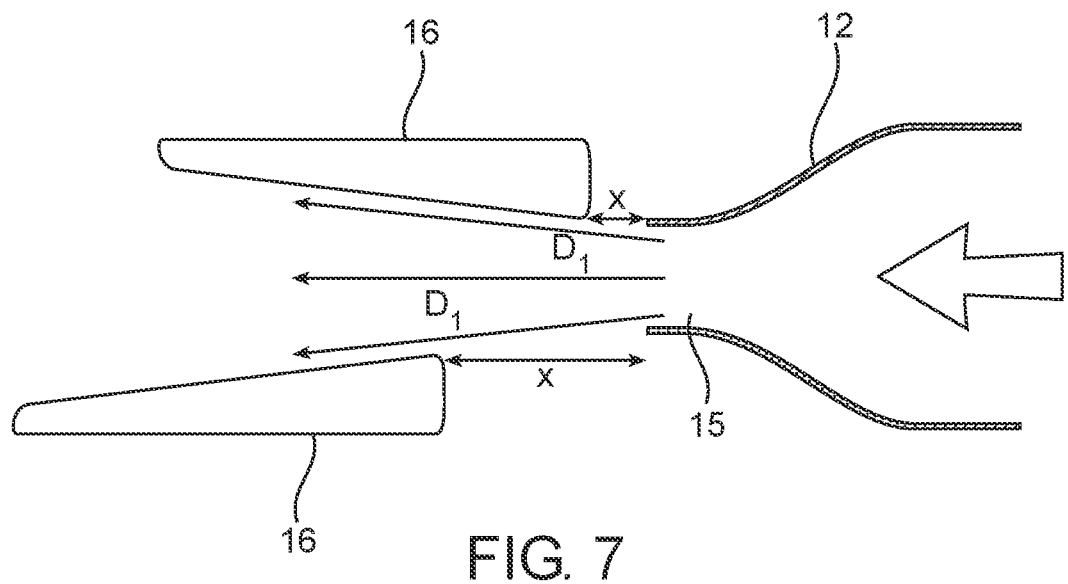

FIG. 7 shows a manner for selecting the diameter D1 at entry of the downstream component 16 relative to the distance x from outlet 15 of upstream component 12 so as to receive all the fluid jetted from outlet 15. As shown, D1 is greater for larger distances x to ensure receipt of the fluid jetted from upstream component 12.

Figure 8:
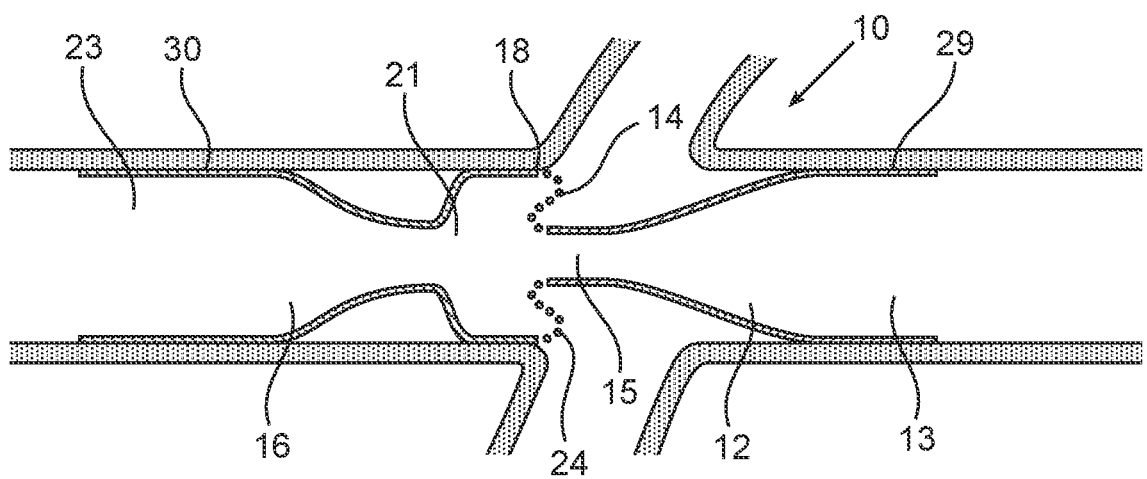

FIG. 8 illustrates fluid modulator 10 constructed similarly to fluid flow modulators 10 of FIGS. 2 and 3A, although gap 14 is along a portion that extends radially outward from outlet 15 of upstream component 12. Gap 14 is formed along a curved portion (e.g., S-shaped) between fluid flow structure 18 and outlet 15. This curved portion allows downstream component 16 to be close to the branched lumen(s). In addition, fluid flow structure 18 is positioned downstream from the intersection between the branched lumen(s) and the body lumen for simplicity and additional anchoring support. Fluid modulator 10 may be formed from a common frame (e.g., a single stent design), which facilitates control of the distance x between outlet 15 and entry 21. A single structure also facilitates co-axial orientation, especially for eccentric upstream and downstream components.

Figure 9:
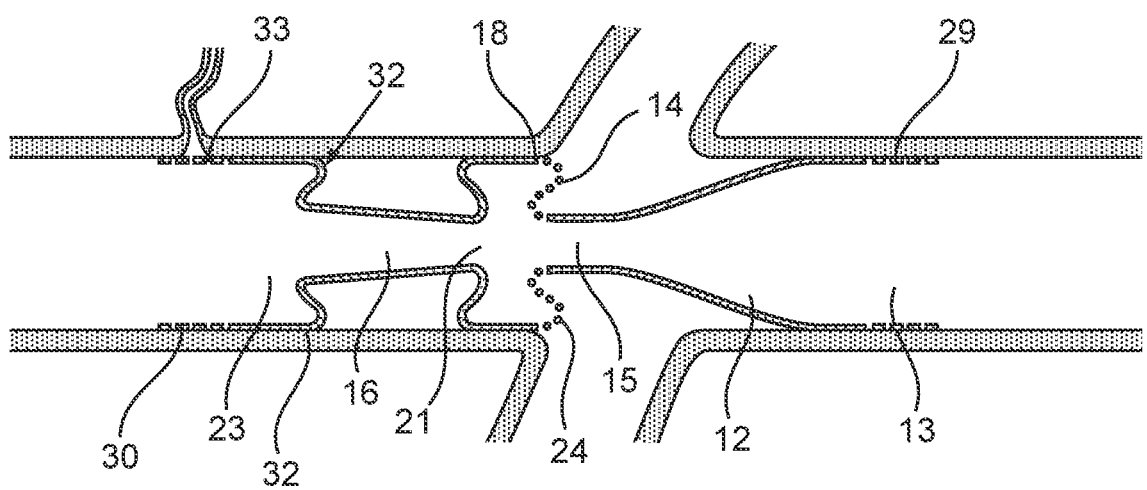

FIG. 9 illustrates flow modulator 10 constructed similarly to flow modulator 10 of FIG. 8, although downstream component 16 includes curved portion 32 (e.g., S-shaped) that extends radially outward to contact the inner wall of the body lumen. A second curved portion downstream in downstream component 16 provides further radially force to enhanced anchoring within the body lumen and also gives a longer diffuser for a given length. Flow modulator 10 also may include an additional gap(s) so as to not block fluid flowing from other branched vessels, such as gap 33 at the downstream end of downstream component 16.

Figure 10:
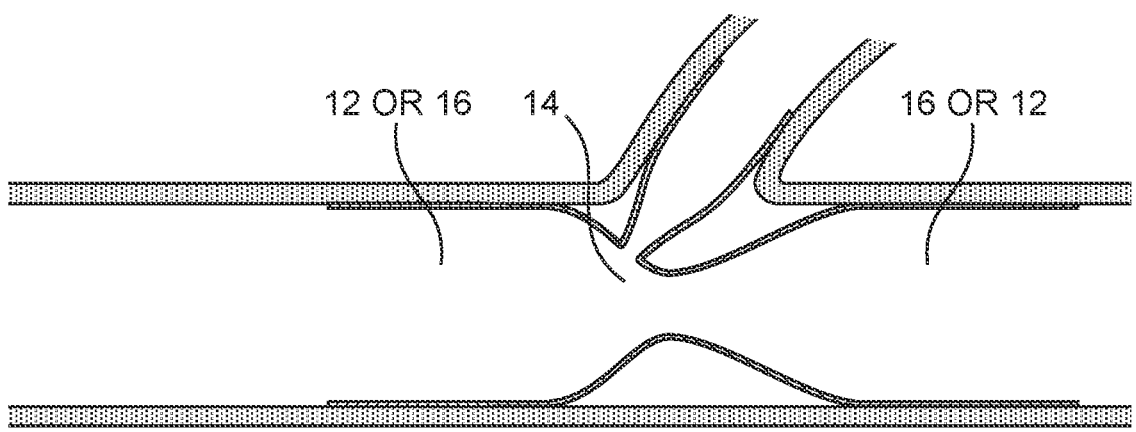
Figure 11:
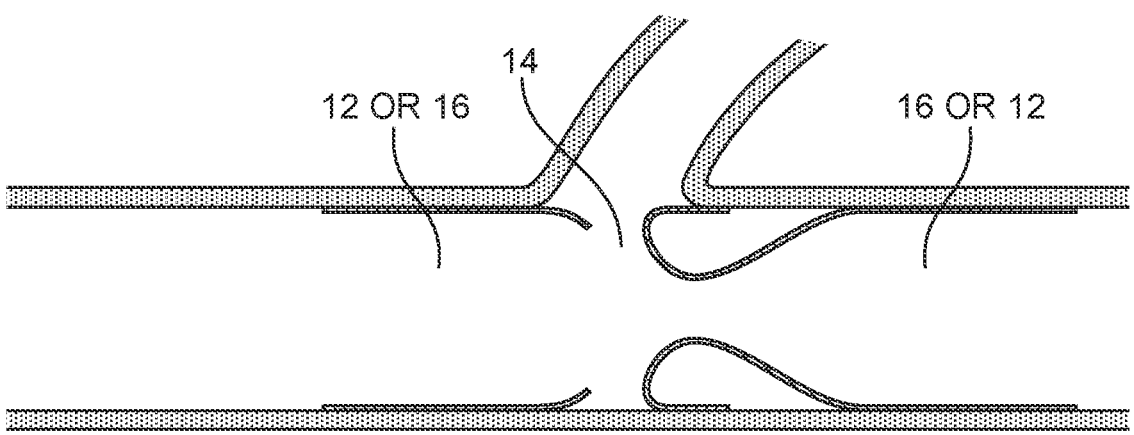

Reference is now made to FIG. 10 and FIG. 11, which illustrate flow modulators 10 with gap 14 positioned asymmetrically with respect to upstream component 12 and downstream component 16. In other words, gap 14 is not positioned along the axis of the major vessel between upstream component 12 and downstream component 16, but instead is offset towards one of upstream component 12 and downstream component 16.

The left side structure of FIGS. 10 and 11 may be the upstream or downstream direction, depending on the application; thus, the left side structure is labeled 12 or 16 and the right side structure is labeled 16 or 12.

Figure 12:
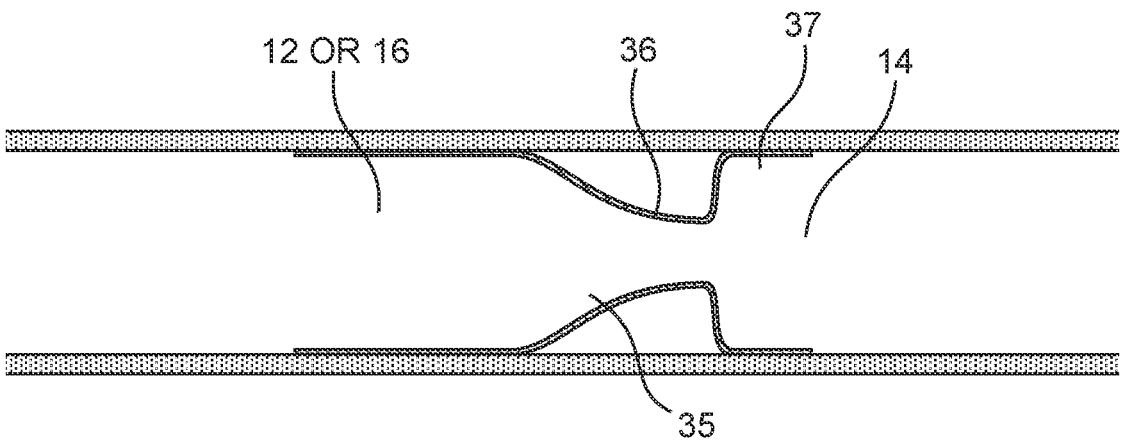

FIG. 12 illustrates a construction of either upstream component 12 or downstream component 16, depending on the direction of flow. The structure includes relatively wide portion 35 which converges into relatively narrow portion 36. Relatively narrow portion 36 extends into diverging portion 37 which serves as a sealing portion.

Figure 13:
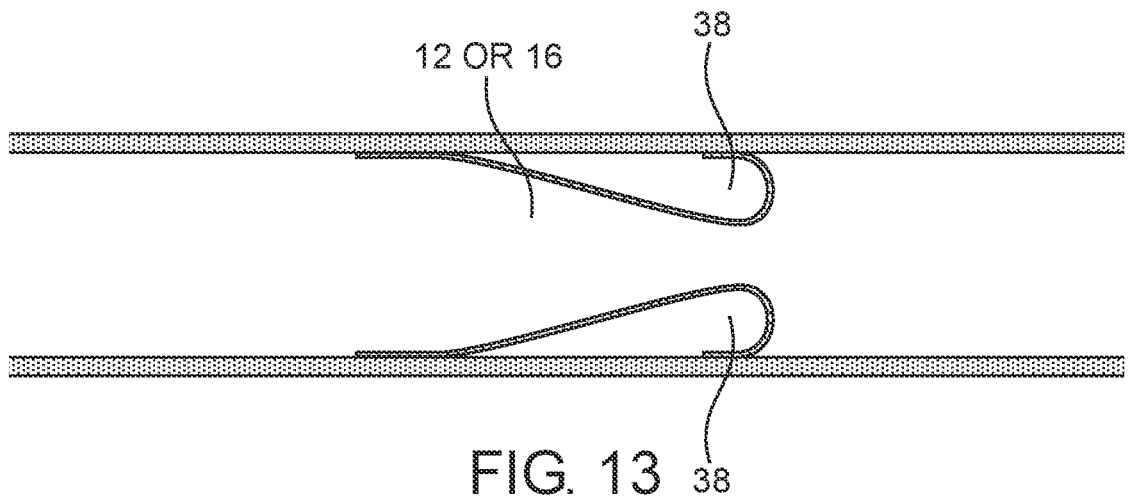

FIG. 13 illustrates another construction of either upstream component 12 or downstream component 16, depending on the direction of flow. The structure of converging portion 38 includes surfaces that curve backward in the opposite direction.

Figure 14A:
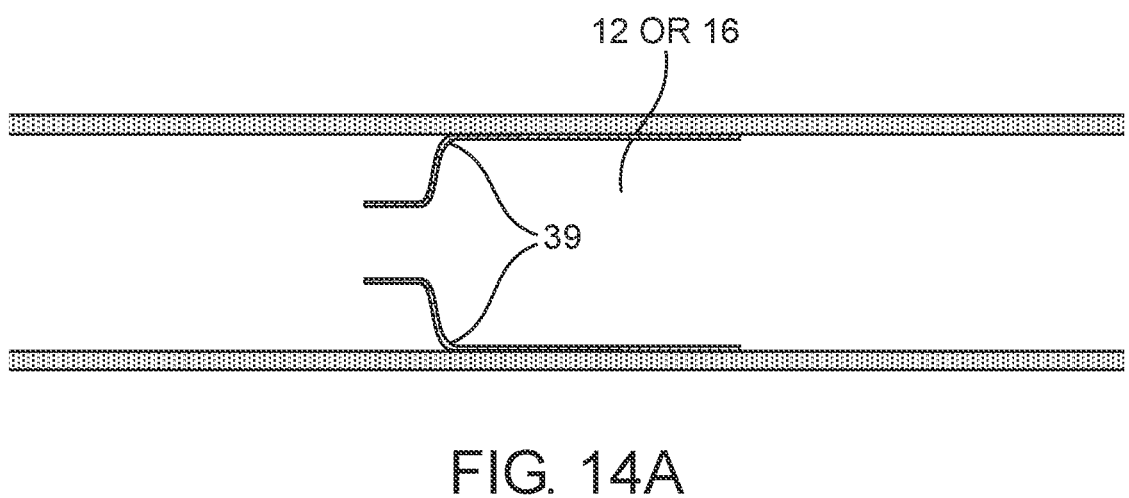
Figure 14B:
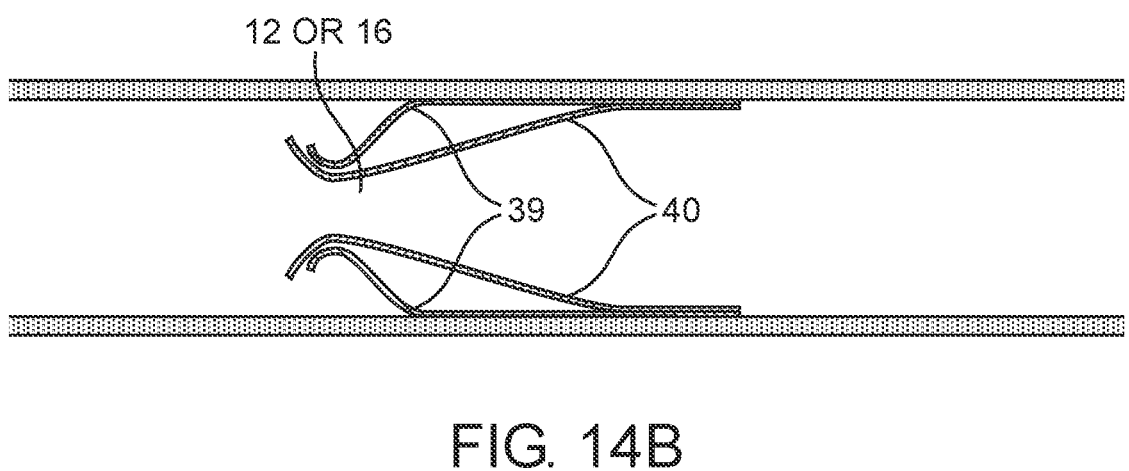

FIGS. 14A and 14B illustrate another construction of either upstream component 12 or downstream component 16. In this construction, first stent member 39 may be installed with converging and diverging portions (FIG. 14A) and afterwards second stent member 40 may be installed over first stent member 39 to define a final converging and diverging shape. FIG. 14A may also be used as is, without the additional stent member. It is noted that the first stent member does not have to touch the second stent member (diffuser stent) and can be shorter than that shown in the drawings.

Figure 15:
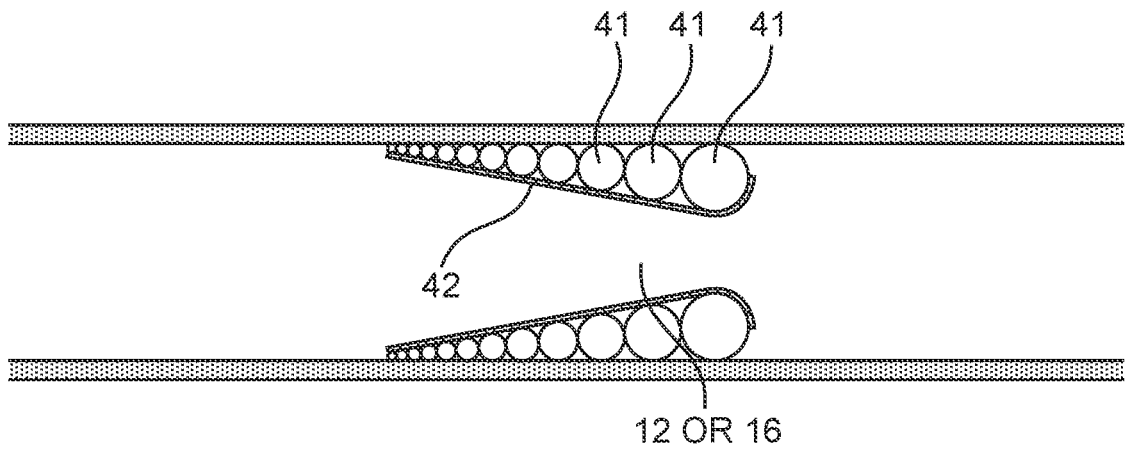

FIG. 15 illustrates an alternative design in which upstream component 12 is constructed of a plurality of discrete objects 41, such as but not limited to, spheres, balloons, rods, and the like, which gradually increase in size to create the converging effect. Similarly, downstream component 16 may be constructed of a plurality of discrete objects 41, such as but not limited to, spheres, balloons, rods, and the like, which gradually decrease in size to create the diverging effect. Discrete objects 41 may be optionally covered with membrane 42 to provide a smooth flow surface.

Figure 16:
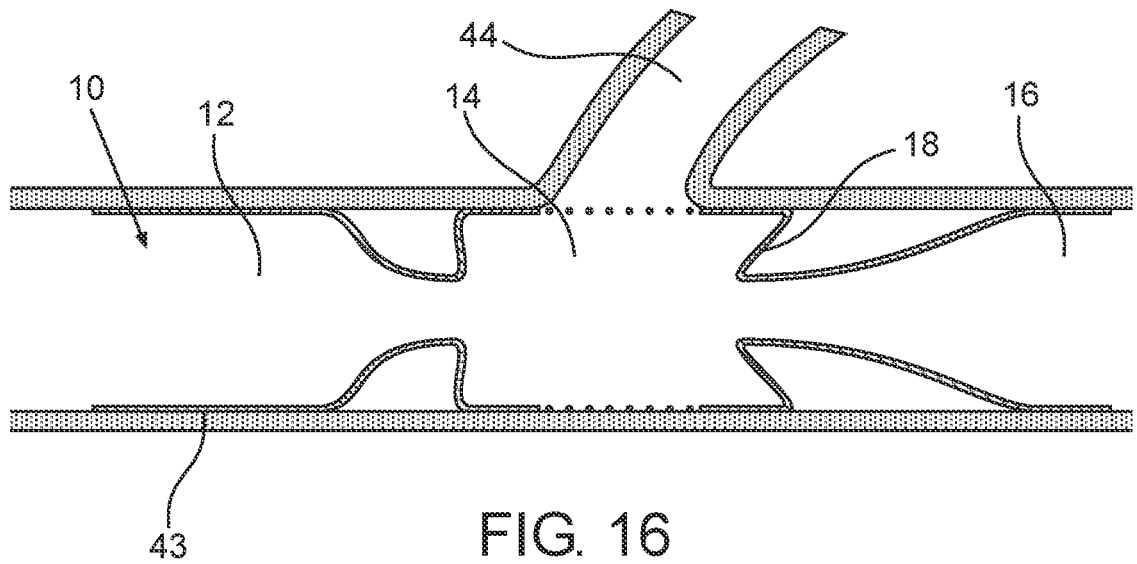

FIG. 16 illustrates flow modulator 10 of FIG. 2 installed in a body lumen 43, such that gap 14 is situated at a bifurcation 44.

Figure 17:
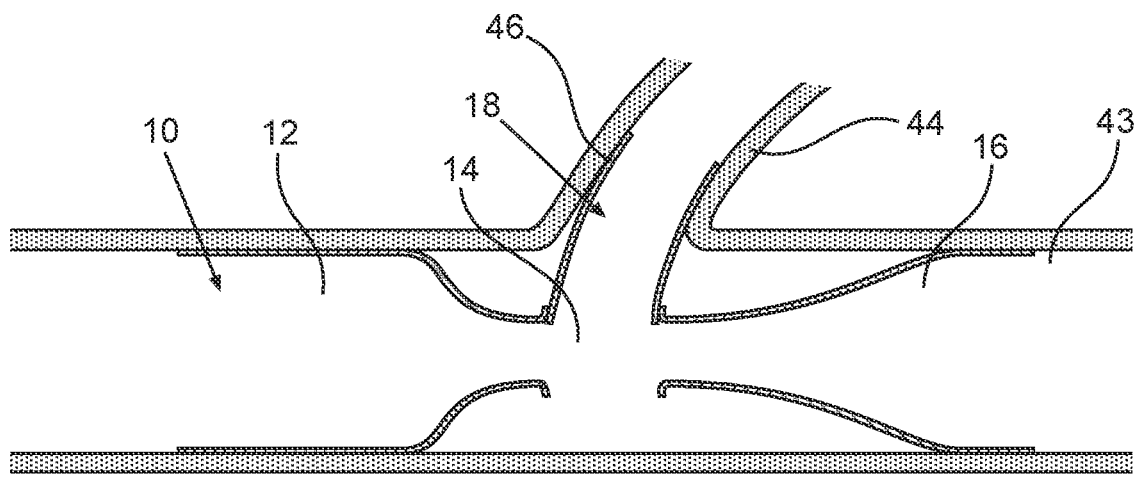

FIG. 17 illustrates another embodiment of flow modulator 10 installed in the body lumen 43, such that gap 14 is situated at bifurcation 44. In this embodiment, fluid flow structure 18 includes extension 46 that is deployed in bifurcation 44. The opening in the stent graft at the bottom of the device (in the sense of FIG. 17; of course, it could be situated in a different location other than "bottom"), may be used instead of sleeve-like extension 46. Alternatively, extension 46 may be used both at the top and the bottom, or an opening may be used at the top and bottom or any other combination.

Figure 18:
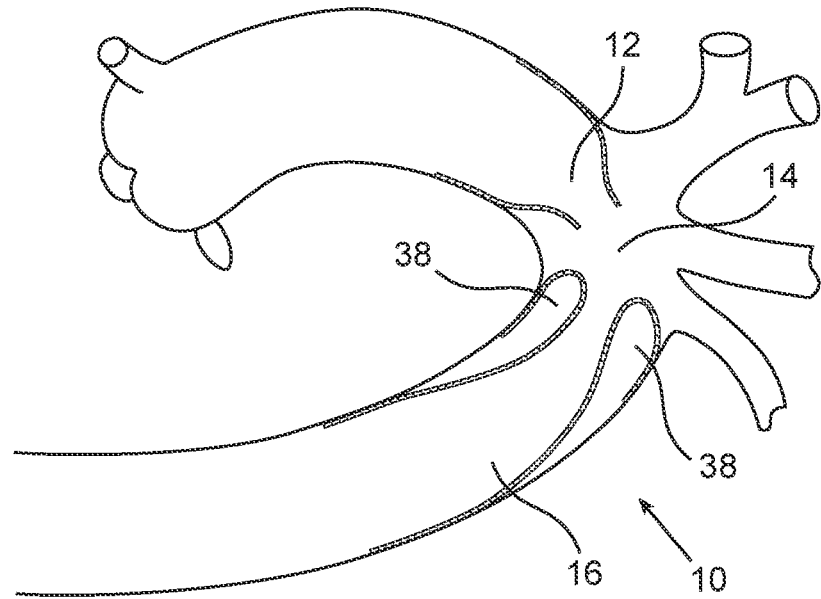

FIG. 18 illustrates the flow modulator of one of the embodiments installed in the aortic arch, such that gap 14 is situated at the bifurcation of the carotid arteries. This installation may be used to reduce peak pressure gradients or to divert emboli away from the carotid arteries with very little pressure loss.

Figure 19:
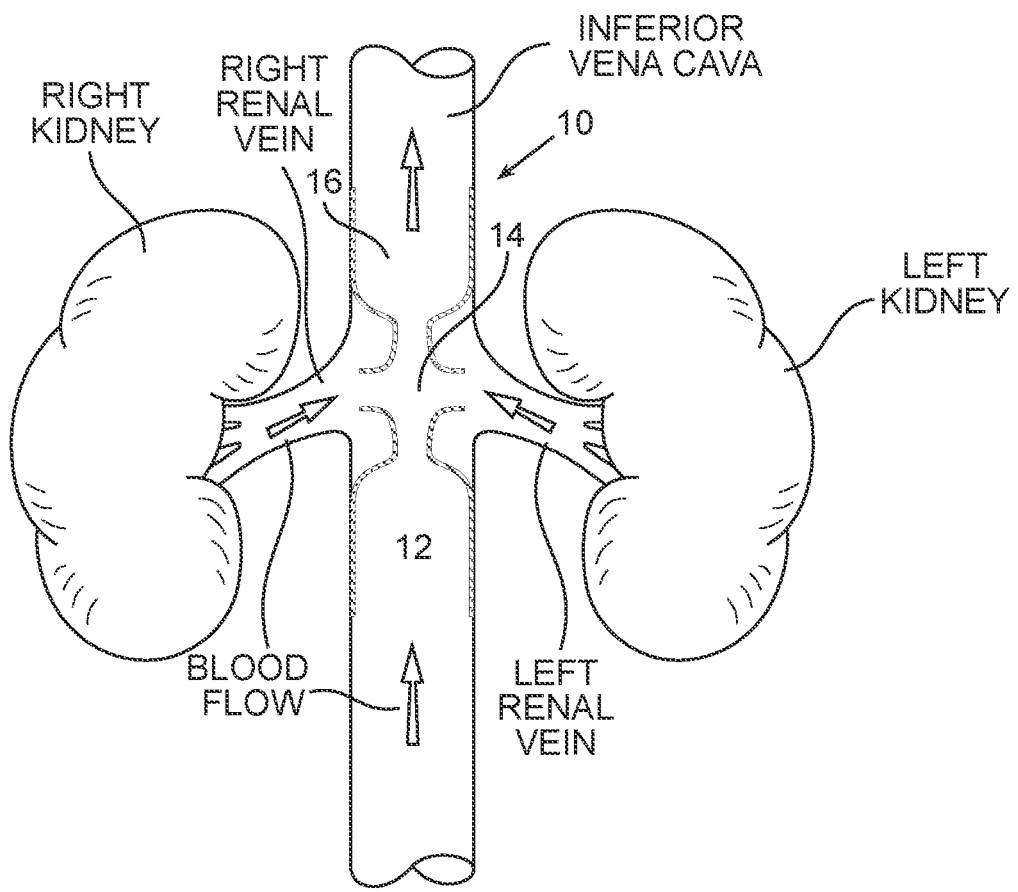

FIG. 19 illustrates a flow modulator installed near the kidneys. For example, upstream component 12 may be installed in the inferior vena cava just below (upstream to) the branch off to the renal vein and the downstream component 16 may be installed in the inferior vena cava just above (downstream to) the branch off to the renal vein. Gap 14 is at the branch to the renal vein. Flow modulator 10 creates a reduced pressure region in the vicinity of gap 14 and increases blood flow velocity at gap 14. Entrainment may also help draw blood into the gap from the kidneys. In this manner, the invention can draw blood from the kidneys to the renal veins and then to the inferior vena cava, thereby improving kidney functionality and reducing necrotic damage to the kidneys.

Figure 20:
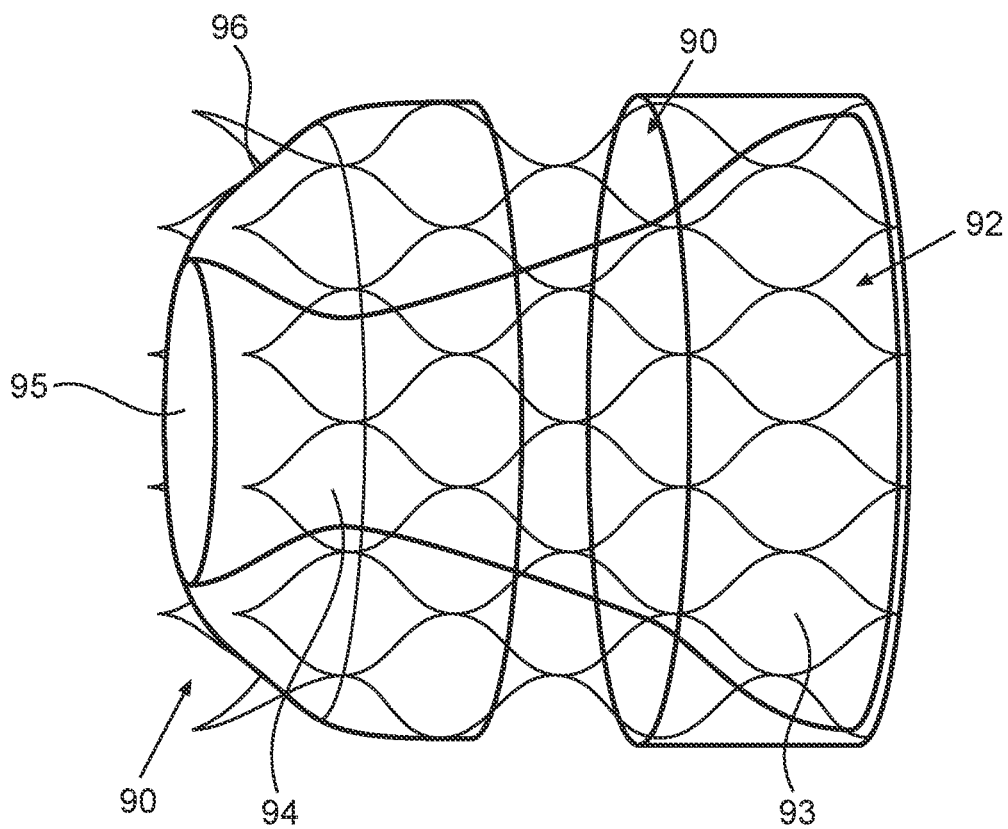
FIGS. 20 and 21 are side views of illustrative flow accelerators constructed in accordance with the principles of the present invention.

Reference is now made to FIG. 20, which illustrates another construction of either upstream component or downstream component, depending on the direction of flow. The structure includes outer stent 90 and inner stent 92. Outer stent 90 may be cylindrical. Inner stent 92 may include relatively wide portion 93 which converges into relatively narrow portion 94. Relatively narrow portion 94 extends into slightly diverging portion 95 with very little energy losses. The two stents may be joined together (such as, but not limited to, by welding or other suitable technique) and at least partially coated with coating 96 (although they may be used as bare metal, uncoated stents as well). The order of the joining and coating processes may be joining before coating or coating before joining.

Figure 21:
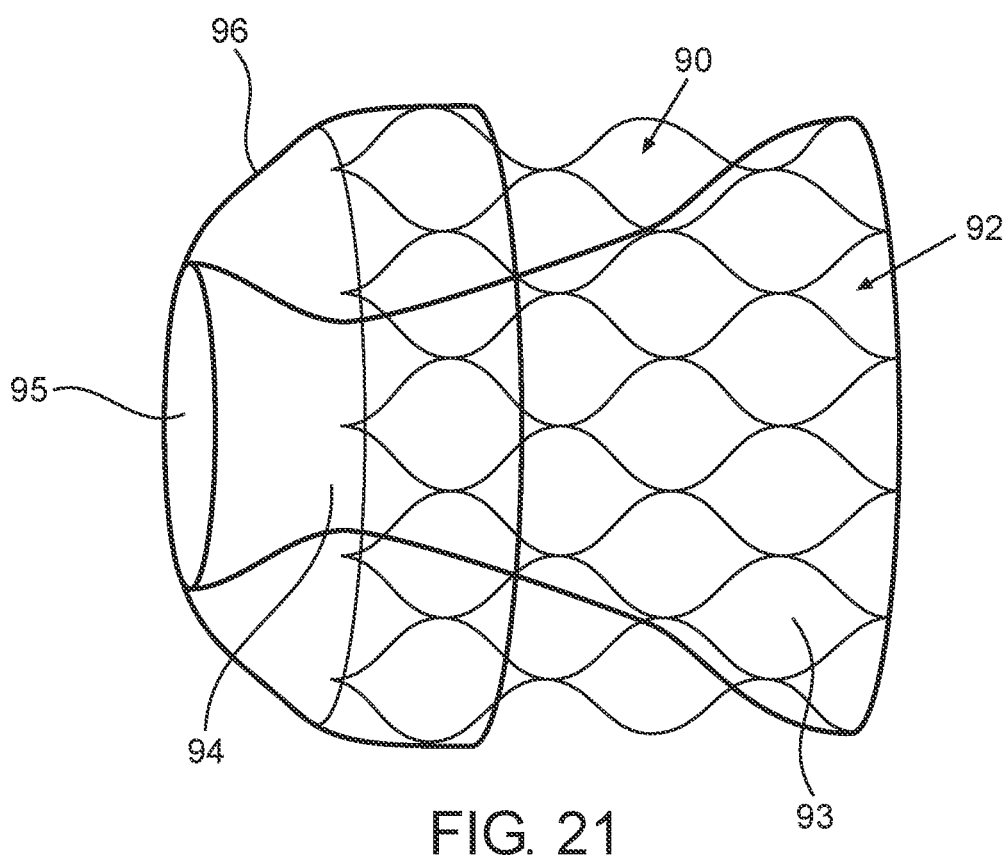

Reference is now made to FIG. 21, which illustrates another version of the embodiment of FIG. 20. In this version, outer stent 90 is shorter so that coating 96 coats over the end of outer stent 90.

Figure 22:
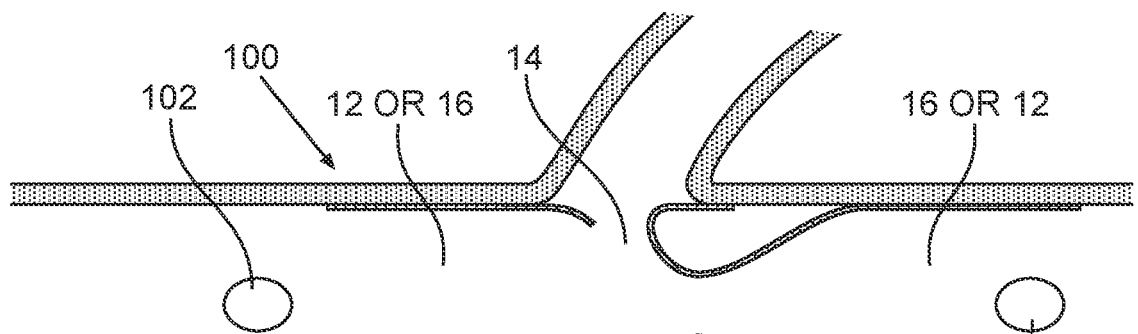
FIG. 22 is a schematic view of a fluid flow modulator, in accordance with another non-limiting embodiment of the present invention, and including a pump (either downstream or upstream)

Reference is now made to FIG. 22, which illustrates flow modulator 100, in accordance with another non-limiting embodiment of the present invention. Flow modulator 100 includes pump 102, such as but not limited to, an axial flow pump, centrifugal pump, booster pump, chopper pump and many others. Pump 102 may be secured in place by a stent or may be coupled to a portion of the upstream component 12 or downstream component 16. Pump 102 may be located either downstream or upstream, depending on the particular application. Pump 102 may be used to augment blood flow and filtration, for example.

Any of the embodiments of the invention may serve to divert emboli or other debris, so there is no need to use an extra filtration device. One example is using the upstream component or downstream component at or near the carotid arteries to divert emboli or other debris.

Figure 23:
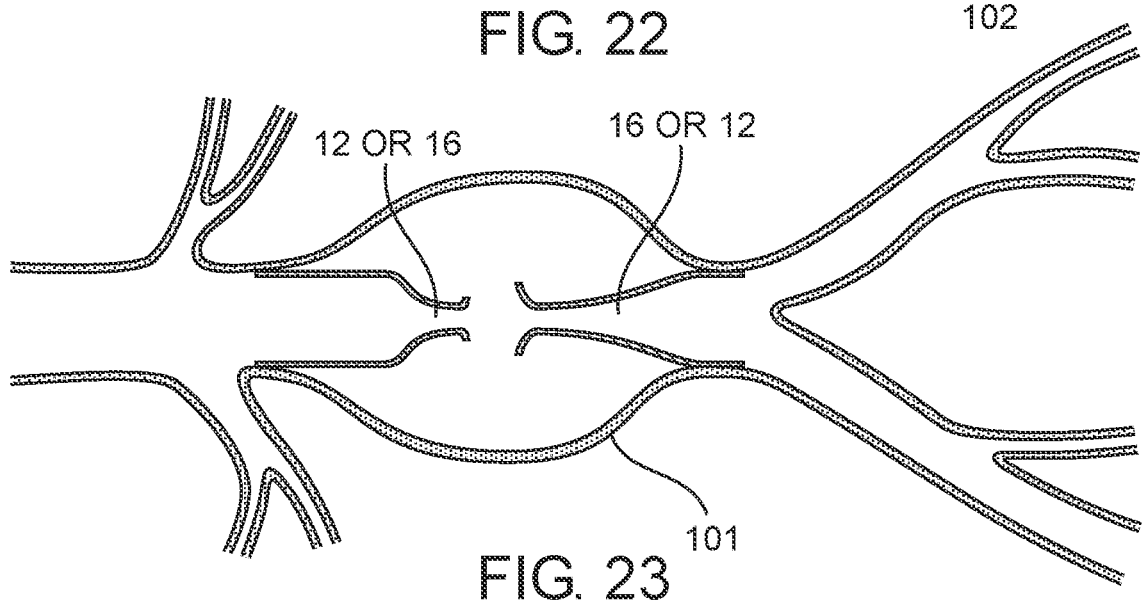
FIG. 23 is a schematic view of a fluid flow modulator installed in an aneurysm, in accordance with a non-limiting embodiment of the present invention.

Reference is now made to FIG. 23, which illustrates flow modulator 10 (or any other flow modulator of the invention) installed in an aneurysm 101. The flow modulator is installed through the blood vessel and lowers pressure at the aneurysm site, so as to help prevent the aneurysm from increasing in size or bursting, and perhaps decreasing the size of the aneurysm. The flow modulator works even without sealing against the aneurysm.

If there are one or more side branch lumens at or near the aneurysm site, the device reduces the pressure but also permits blood to flow to the side branches. This is in contrast to circular stent grafts of the prior art which disadvantageously block the side branches. If there are no side branches, then the device just reduces the pressure without increasing the blood flow.

A filter may be optionally used with the flow modulator to prevent embolic debris from flowing from the aneurysm to other blood vessels.

Figure 24:
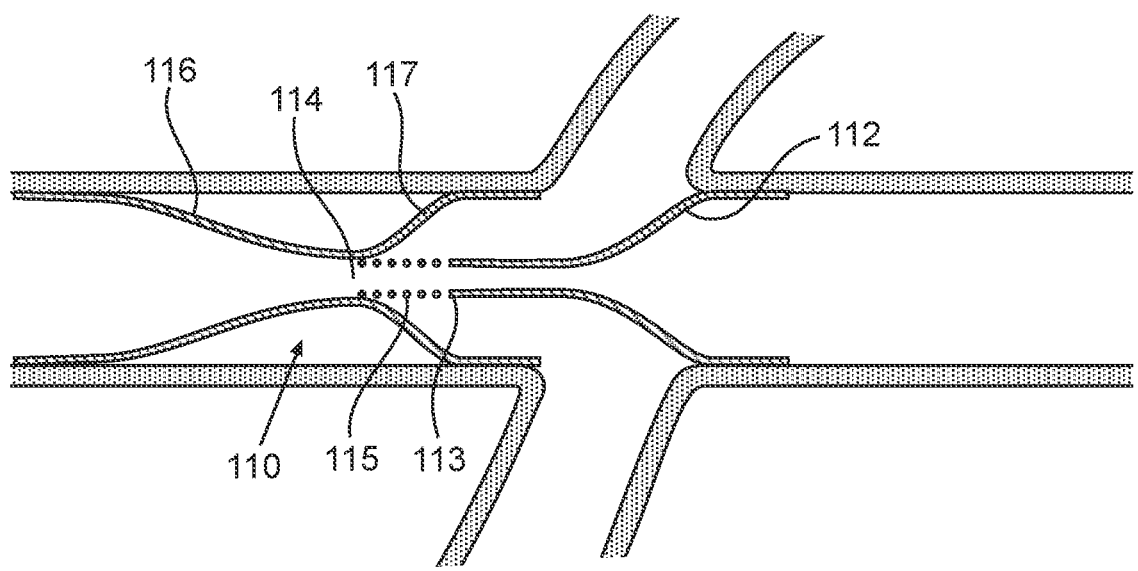
FIG. 24 is a schematic view of a fluid flow modulator, in accordance with another non-limiting embodiment of the present invention, in which an outlet nozzle of an upstream flow accelerator enters a mouth portion of a downstream flow decelerator.

Reference is now made to FIG. 24, which illustrates flow modulator 110, in accordance with another non-limiting embodiment of the present invention. Flow modulator 110 includes upstream component 112 with outlet 113 and downstream component 116 which has an upstream divergent mouth entry 117. Outlet 113 enters entry 117 and this area serves as gap 114. Outlet 113 may be coupled with support 115 to a portion of downstream component 116, for example, to center outlet 113 with respect to entry 117. Alternatively, a separate stent structure (which does not hinder flow) may be used to support outlet 113.

The straight portion in downstream component 116 may help straighten the flow before it is diffused and reduce flow separation form the diffuser wall, thereby reducing pressure losses.

FIG. 24 shows one example of flow modulator 110 installed in a renal application. In this example, upstream component 112 may be installed in the inferior vena cava upstream to the branch off to the renal vein and the downstream component 116 may be installed in the inferior vena cava downstream to the branch off to the renal vein. Outlet 113 is also downstream to the branch off to the renal vein. Similar to the embodiment of FIG. 19, flow modulator 110 creates reduced pressure at outlet 113 in gap 114, which increases blood flow velocity from the renal vein to the gap.

Figure 25:
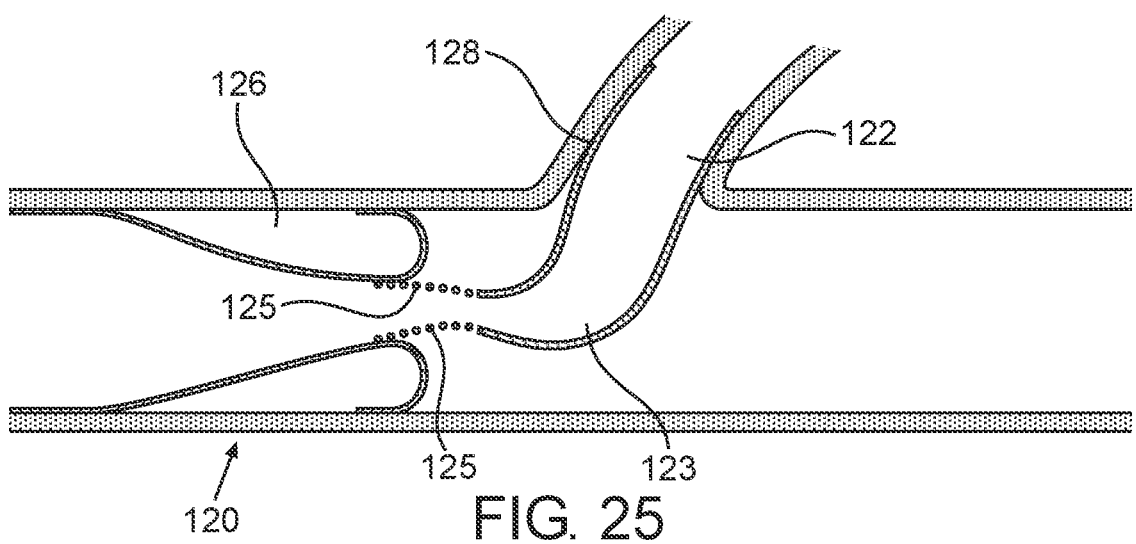
FIG. 25 is a schematic view of a fluid flow modulator, in accordance with another non-limiting embodiment of the present invention, with an upstream flow accelerator that has a portion which is not in-line with a downstream flow decelerator, but is instead tilted relative thereto and which may be installed in a branch lumen.

Reference is now made to FIG. 25, which illustrates flow modulator 120, in accordance with another non-limiting embodiment of the present invention. Flow modulator 120 includes upstream component 122 with outlet 123 and downstream component 126. Upstream component 122 has first portion 128 which is not in-line with downstream component 126, but is instead tilted relative thereto and which may be installed in a branch lumen, as shown in FIG. 15. Outlet 123 may be directed to the center of the inlet to downstream component 126. Outlet 123 may be coupled with support 125 to a portion of downstream component 126, for example, to center the nozzle with respect to the inlet. Alternatively, a separate stent structure (which does not hinder flow) may be used to support outlet 123.

Figure 26:
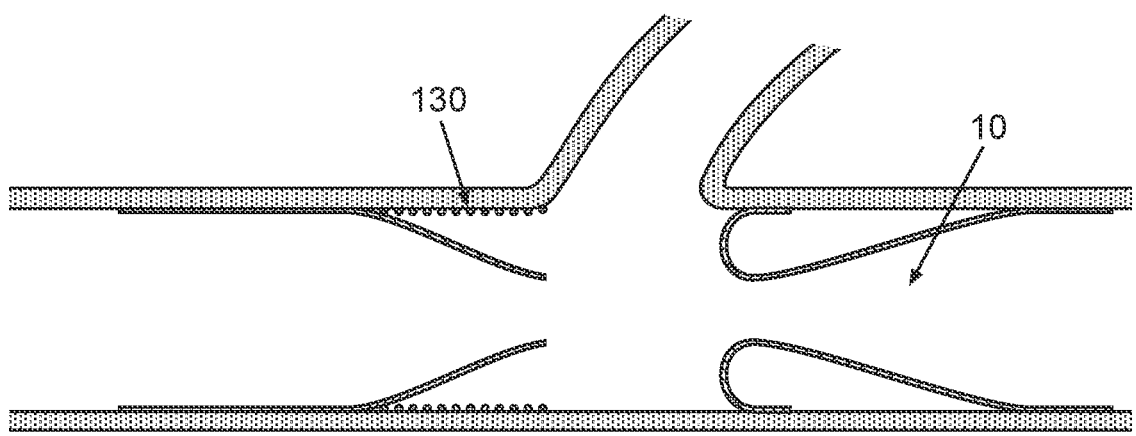
FIG. 26 is a schematic view of a lumen support member used with a fluid flow modulator, in accordance with another non-limiting embodiment of the present invention.

Reference is now made to FIG. 26, which illustrates lumen support member 130 installed with flow modulator 10, in accordance with another non-limiting embodiment of the present invention. Lumen support member 130, which may be a stent body, helps support the body lumen from collapsing inwards during reduced pressure.

Figure 27:
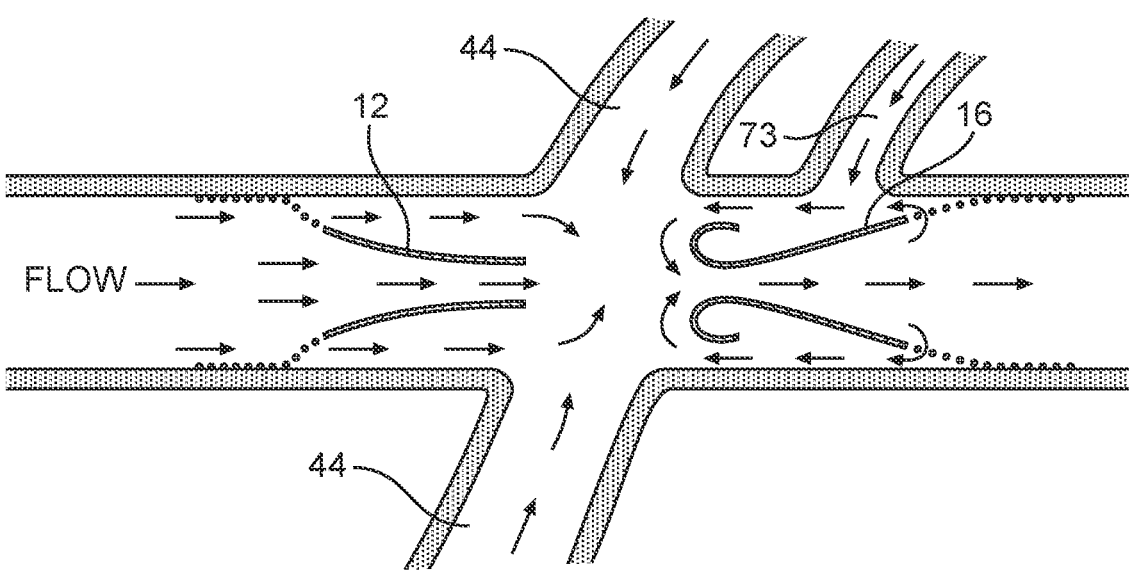
FIG. 27 is a schematic view of a fluid flow modulator, in accordance with another non-limiting embodiment of the present invention, in which the upstream flow accelerator and/or downstream flow decelerator may not seal against the inner contour of the body lumen.

Reference is now made to FIG. 27, which illustrates that in any of the embodiments, upstream component 12 and/or downstream component 16 may not seal against the inner contour of the body lumen, but instead may be spaced from the inner contour of the body lumen. For example, this arrangement prevents blocking flow from a side branch 73. Although this may create pressure losses, it still reduces pressure as compared to just using a nozzle, and it may improve flow out of the body lumen, such as improving flow out of a vein.

Figure 28:
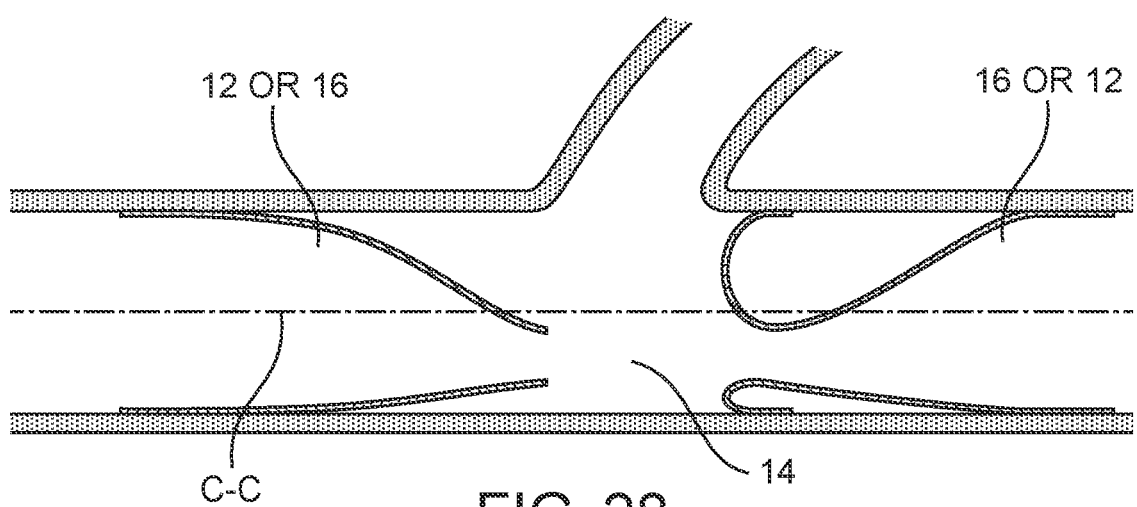
FIG. 28 is a schematic view of an asymmetric transition between the upstream flow accelerator and the downstream flow decelerator, in accordance with another non-limiting embodiment of the present invention.

Reference is now made to FIG. 28, which illustrates that the transition between upstream component 12 to downstream component 16 (the region of gap 14) may be off-center from the center line C-C of the body lumen. In such an embodiment, the transition between upstream component 12 to downstream component 16 is asymmetric with respect to the center line of the body lumen. For example, this may be used advantageously if there is only one side branch—the asymmetry will favor flow from the side branch; if there are two side branches, the asymmetry will favor flow from one of the side branches.

Figure 29A:
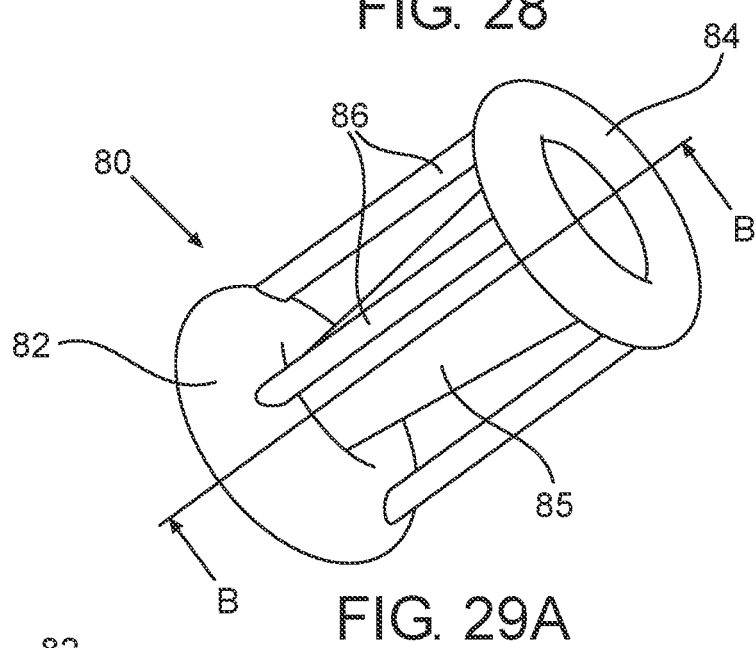
Figure 29B:
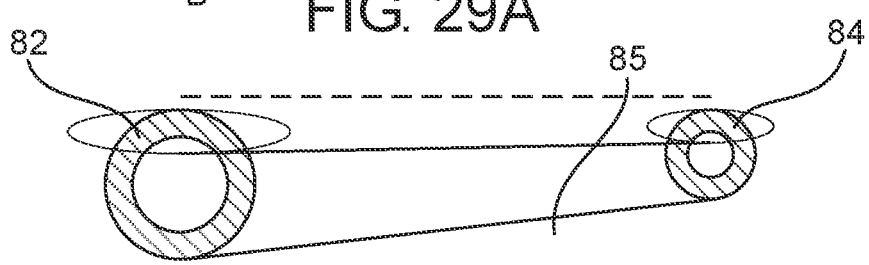
Figure 29B:
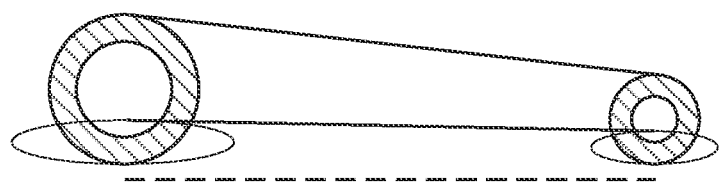

Reference is now made to FIGS. 29A and 29B, which illustrate upstream component or downstream component 80, whose shape is changeable in accordance with another non-limiting embodiment of the present invention. Upstream component and downstream component 80 may be combined to create a nozzle/diffuser configuration with a gap therebetween similar to the structures described throughout this disclosure.

Accelerator or decelerator 80 may include one or more inflatable members, such as end faces 82 and 84 coupled by intermediate member 85, such as but not limited to, inflatable balloons or bladders, which can be inflated or deflated by introducing or extracting fluid into or from inflatable members 82 and 84 (connected to a suitable fluid source, such as water, saline, air, etc. Intermediate member 85 may be a cover material and/or may be pre-shaped (e.g., a cylindrical shape like a stent) thereby creating radial force on inflatable members 82 and/or 84 to create better sealing. Changing the size of inflatable members 82 and 84 changes the flow characteristics through the device. For example, one can change how much the device diverges or converges. Inflatable members 82 and 84 may be connected by longitudinal members 86, which may also be inflatable and thus changeable in size, such as changeable in length or thickness.

The device may be deployed in the deflated state and then inflated in-situ. In the example where the upstream component and the downstream component are combined into one device, the respective inflatable members may be inflated/deflated simultaneously with a common lumen in a catheter or individually using a multi-lumen catheter. After the patient has reached a stable condition, the device may be deflated or inflated as needed to adapt to changing conditions. The device may be deflated for removal from the body. A reservoir of fluid may be implanted with the device for use in inflating the device after installation in the body. The device may be held against the inner walls of the body lumen or may be separated from them, as described above for other embodiments.

As is explained above, flow modulator 10 is sized and shaped to be implanted in a body lumen. Flow modulator 10 may be compressible for delivery (e.g., percutaneous delivery within a delivery sheath) and expandable upon deployment (e.g., self-expanding upon exposure from the distal end of the delivery sheath or balloon expandable).

Referring now to FIG. 30, flow modulator 10 is shown in the compressed, delivery configuration within sheath 150 in accordance with another non-limiting embodiment of the present invention. Flow modulator 10 may be coupled to transition portion 152 and/or wire 154 to facilitate delivery to the body lumen and retrieval from the body lumen. Transition portion 152 illustratively has a non-concentric cone shape to facilitate compression into sheath 150 and is coupled to upstream component 12 although it may be coupled to downstream component 16. Wire 154 is coupled to transition portion.

FIGS. 31A and 31B show flow modulator 10 in the expanded, deployed configuration outside of sheath 150. Flow modulator 10 may transition to the expanded, deployed configuration when exposed past the distal end of sheath 150. For example, sheath 150 may be pulled proximally against a fixed stopper in sheath 150 to unsheath flow modulator 10 at a target location within a body lumen, e.g., where the renal veins intersect with the inferior vena cava.

Flow modulator 10 may be retrieved from the body lumen (e.g., inferior vena cava). For example, a sheath may be threaded over wire 154 and wire 154 may be fixed in place (e.g., ex vivo fixation of the proximal end of the wire). Then, the sheath is pushed against transition portion 152 to compress flow modulator 10 within the sheath. Flow modulator 10 and the sheath are then removed from the patient.

Referring now to FIG. 32, flow modulator 10 is shown in accordance with another non-limiting embodiment of the present invention. Flow modulator 10 is similar to flow modulator 10 of FIG. 3A, although flow modulator 10 of FIG. 32 further includes retrieval mechanism 160. Retrieval mechanism 160 may be coupled to the proximal end of upstream component 12 as illustrated. In this manner a retrieval device, e.g., hook 166, may be coupled to retrieval mechanism 160 to pull retrieval mechanism towards sheath 164 to compress flow modulator 10 into sheath 164 for retrieval. For example, retrieval mechanism 160 may be configured like a snare with a plurality of arms coupled to the end of upstream component 12 and coupled together near the center of the flow path within upstream component 12. Flow component 10 may be implanted with retrieval mechanism 160 coupled thereon or retrieval mechanism 160 may be coupled to flow modulator 10 during the retrieval process. Flow modulator 10 in FIG. 32 also includes retrieval mechanism 162 at an opposing end of flow modulator, e.g., coupled to the end of downstream component 16. Retrieval mechanism 162 works in the same manner as retrieval mechanism 160. Use of two retrieval mechanisms may be particularly helpful when flow modulator 10 is formed from a braided structure since the diameter of the structure decreases as the braid is lengthened. Retrieval mechanisms 160 and/or 162 may also be used for partial retrieval. For example, retrieval mechanism 160 and/162 may be pulled (simultaneously or at different times) in a direction(s) away gap 14 to partially or fully reduce the diameter of flow modulator 10 within a body lumen. Such reduction would allow for washing of any stagnant flow zones created adjacent to flow modulator 10. Flow modulator 10 could then be fully removed, repositioned within the body lumen and expanded, or expanded in the prior deployment location within the body lumen.

Figure 33A:
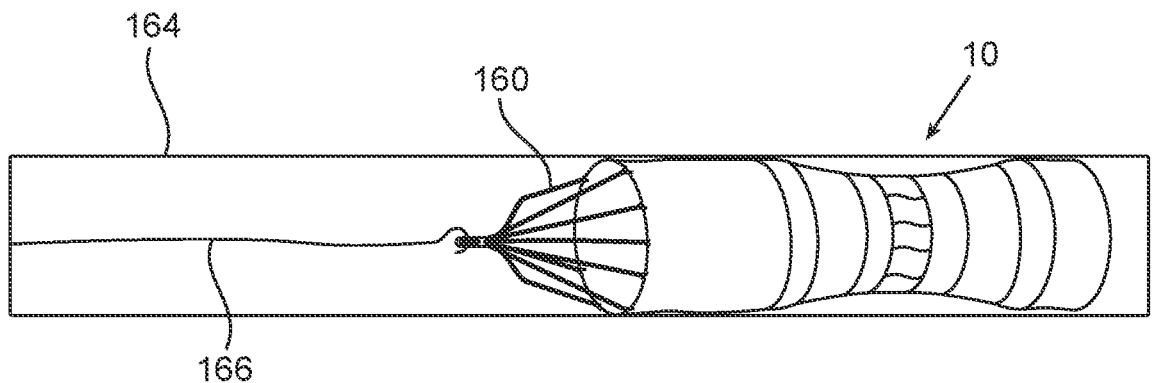
Figure 33B:
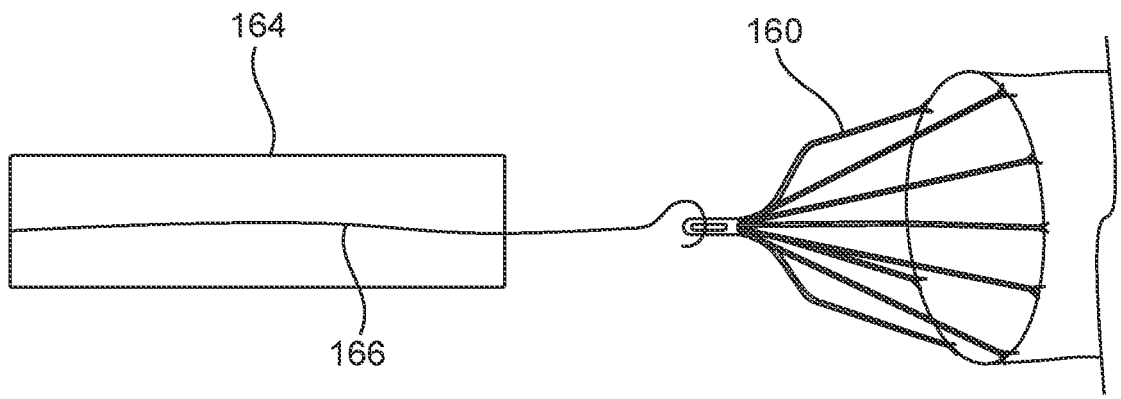

FIGS. 33A and 33B show hook 166 coupled to retrieval mechanism 160 in the compressed state within sheath 164 and in the expanded state outside of sheath 164.

Figure 34:
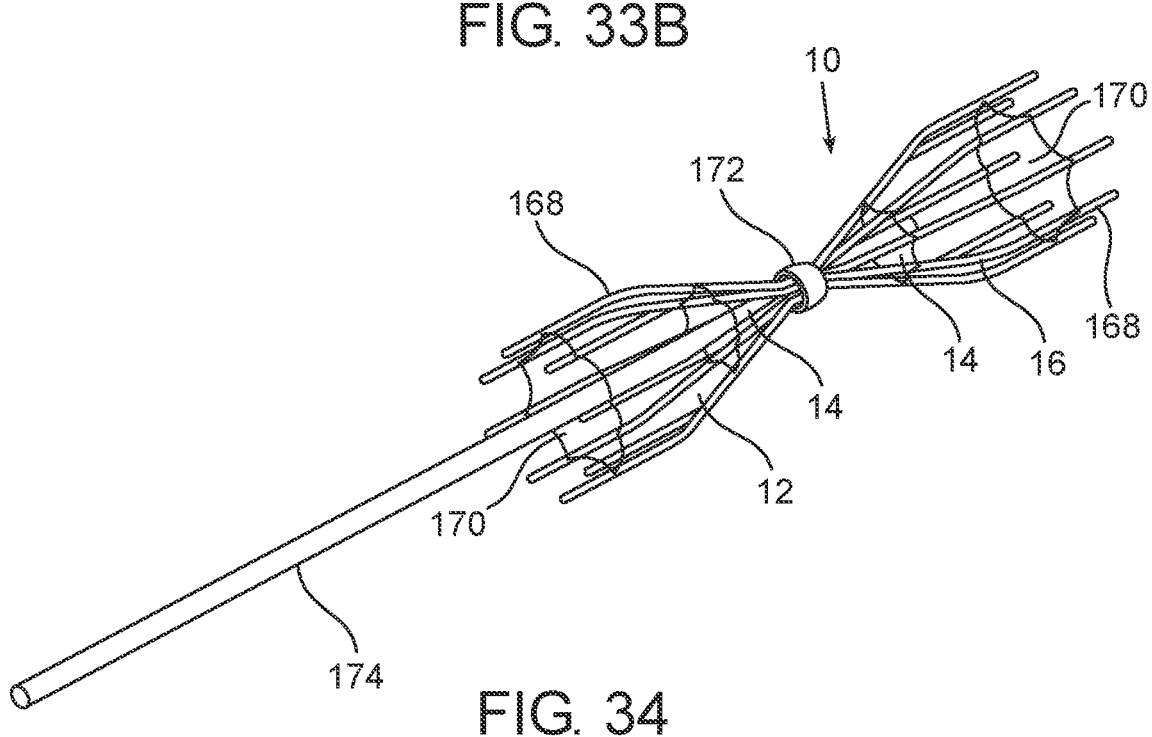

Referring now to FIG. 34, flow modulator 10 is shown in accordance with another non-limiting embodiment of the present invention. Flow modulator 10 is similar to flow modulator 10 of FIG. 3A, although flow modulator 10 of FIG. 34 further includes ring 172. In this illustration, frame 168 is formed from a plurality of ribs and defines upstream component 12 and downstream component 16. Frame 168 may be formed from a shape memory material such as shape memory metal. Frame 168 is coated with biocompatible material 170 at upstream component 12 and downstream component 16 to define the flow channels and the uncoated portion of frame 168 therebetween defines gap 14. Ring 172 is disposed around a portion of frame 168 and maintains the portion disposed therein in a compressed configuration. For example, in the deployed state down in FIG. 34, ring 172 is disposed around the portion of fluid modulator between upstream component 12 and downstream component 16 to cause frame 168 to form a converging cross-sectional flow area at upstream component 12 and a diverging cross-sectional flow area at downstream component 16. Ring 172 is configured to move along frame 168 to transition the portions of frame 168 disposed within ring 172 from an expanded state to a contracted state. Shaft 174 may be coupled to ring 172 such that movement of shaft 174 moves ring 172 along frame 168.

Flow modulator 10 is deliverable in a compressed state within a sheath to a target location within a body lumen. Once suitably positioned, flow modulator 10 is exposed from the sheath (e.g., by pulling the sheath proximally while flow modulator 10 remains in place) and flow modulator 10 self-expands to the deployed configuration. Flow modulator 10 may be partially retrieved (e.g., compressed to allow for washing) and/or fully retrieved by moving ring 172 proximally (e.g., by pulling shaft 174 proximally) to compress upstream component 12 or downstream component 16 to a diameter suitable for insertion within a sheath. The remaining portion of flow modulator 10 may then be compressed within the sheath and removed from the body via the sheath.

Figure 35:
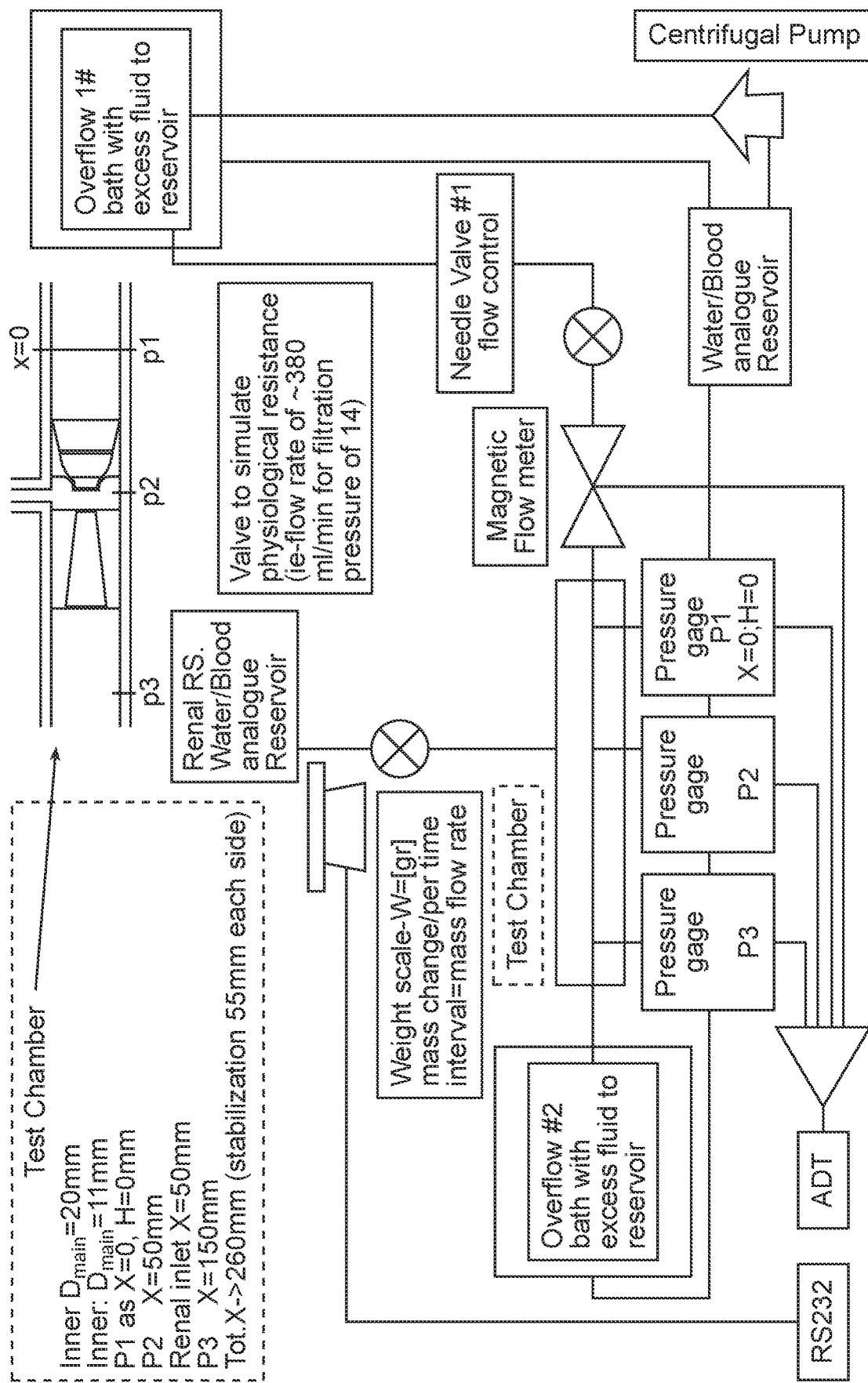
FIGS. 35-37E are the results from a bench top test used for determining preferred configurations for flow modulators constructed in accordance with the present invention.

FIG. 35 illustrates a bench test used for determining the optimal configuration for a flow modulator constructed in accordance with the present invention. In the bench test, a flow modulator was placed in a main lumen (to simulate the inferior vena cava) such that the gap was positioned at a branch lumen (to simulate a renal vein). The bench model utilized a constant steady flow in the main branch and was connected to an over flow bath to maintain constant physiological pressure. Water was used for the fluid and blood analogue was used to verify the trends. A side branch pipe with a controlled resistance was connected to a lifted reservoir (to simulate renal filtration pressure). The resistance in the side branch was fixed in a rate to create a normal renal flow with a normal net filtration pressure. As a result, fluid flow was low when the pressure gradient between the renal bath to the main lumen was smaller.

Three pressure sensors (shown as P1, P2, and P3 in FIG. 35) were connected to the simulated IVC (upstream to the side branch, at the side branch level, and downstream to side branch). A magnetic flow sensor was used to measure IVC flow. Renal flow was measured with a digital weight scale with a computer interface via rs232. Thus, mass flow rate can be measured (or flow rate since the density can be calculated) without creating additional pressure loss.

Figure 36:
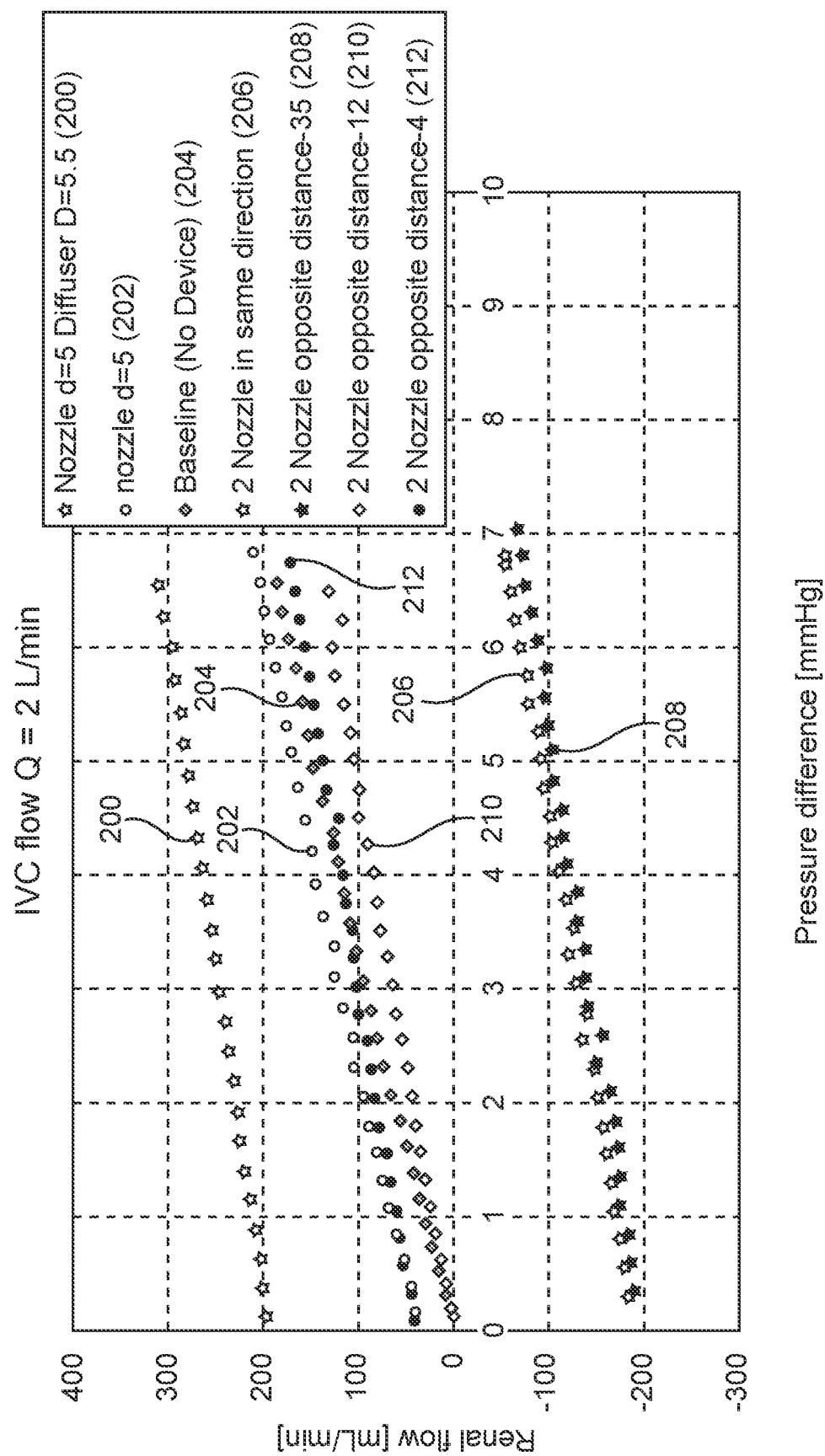
Figure 37A:
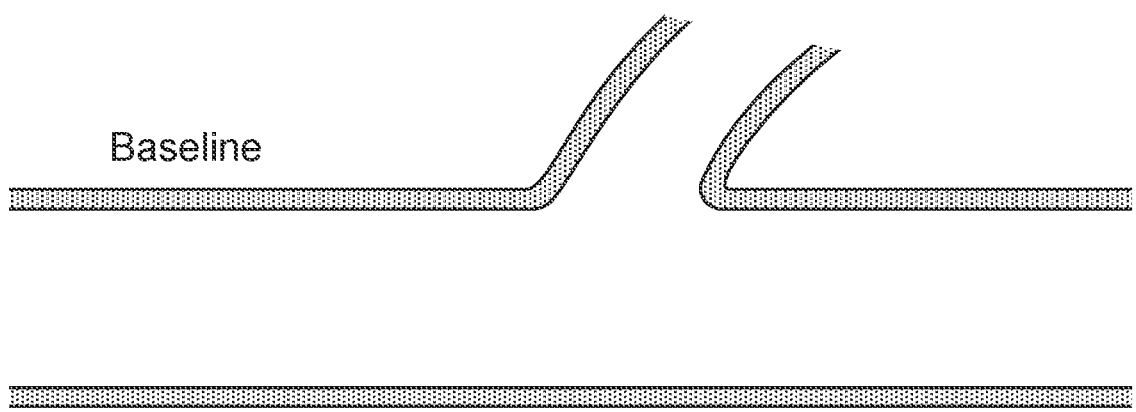
Figure 37B:
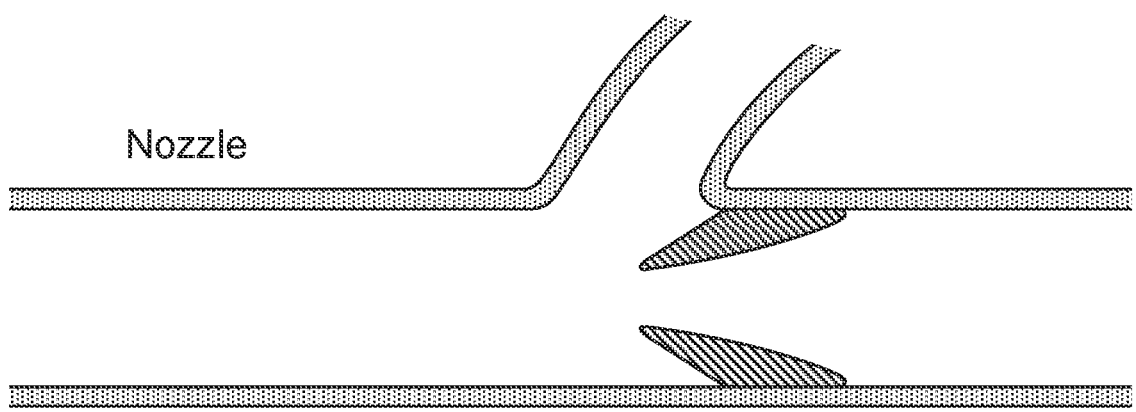
Figure 37C:
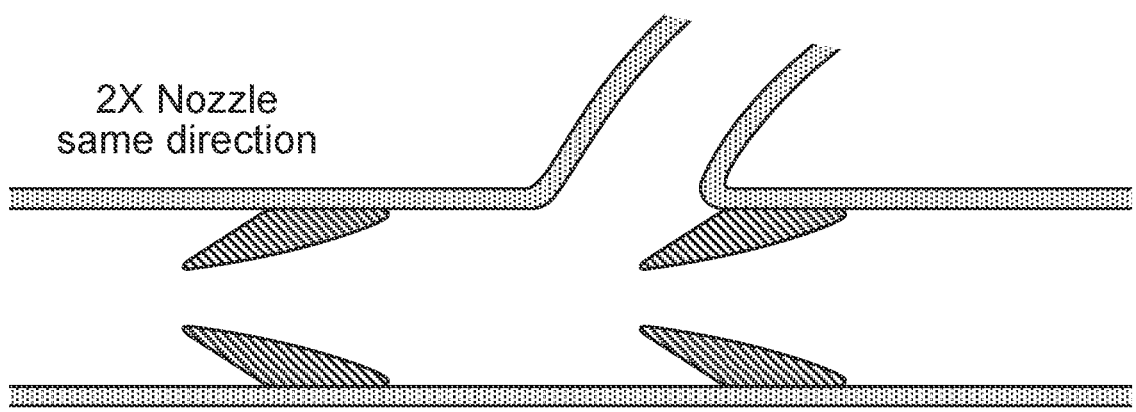
Figure 37D:
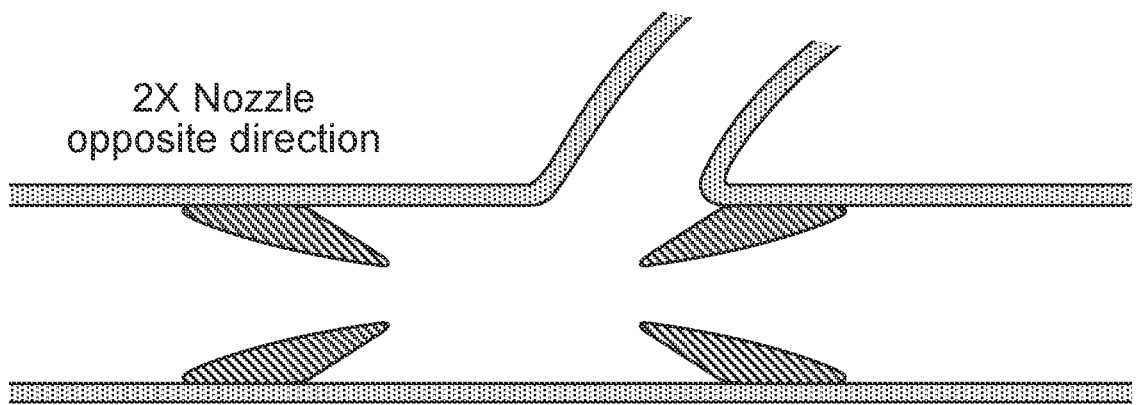
Figure 37E:
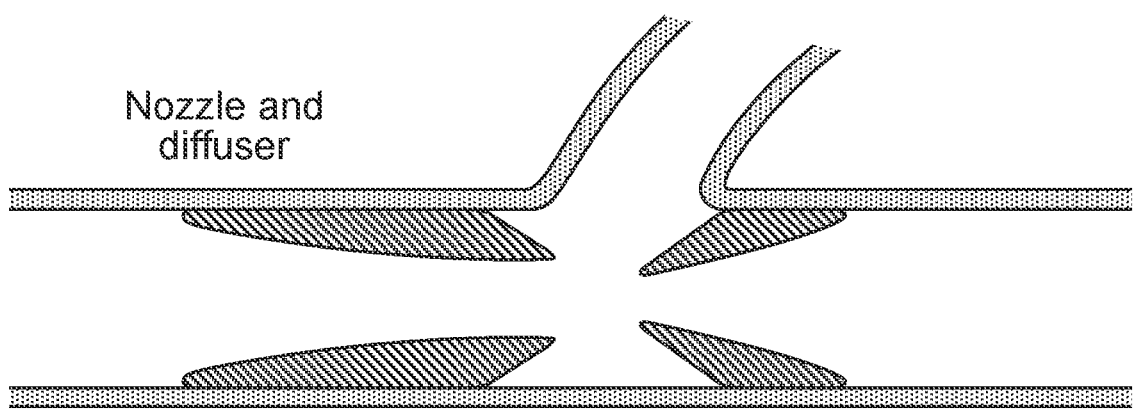

FIG. 36 is a graph showing the results for one representatives IVC flow rate (2 liters per minute (L/min)). The graph shows renal flow in mL/min versus pressure difference in mmHg for various configurations shown in FIGS. 37A-37E. Data points 200 are for a nozzle and diffuser configuration (shown in FIG. 37E) based on the flow modulator principles described herein. In this example, the upstream nozzle has an outlet inner diameter of 5 mm and the downstream diffuser has an entry inner diameter of 5.5 mm. As shown in FIG. 36, the renal flow is highest for this configuration and the table below shows that this nozzle and diffuser configuration create significantly less pressure loss than all other configurations. Data points 202 are for a single nozzle configuration (shown in FIG. 37B). The same upstream nozzle was used as the upstream nozzle in the nozzle and diffuser configuration. As shown in FIG. 36, the renal flow is lower than the nozzle/diffuser configuration, but higher than the other configurations and the pressure loss of 11 mmHg shown in the table below is significantly larger than the pressure loss of the nozzle and diffuser configuration. Data points 204 are for baseline, meaning no device is used (shown in FIG. 37A). As shown in FIG. 36, only the nozzle and diffuser configuration based on the principles of the present invention is significantly better than baseline. Data points 206 are for two nozzles in the same direction (shown in FIG. 37C). As shown in FIG. 36, renal flow is actually negative, which would send blood flow in the renal veins in the wrong direction. In addition, the table below confirms the pressure loss of 22 mmHg is high. The same upstream nozzle was used as above and the downstream nozzle has an outlet inner diameter of 5 mm. Data points 208, 210, and 212 are for two nozzles in opposite directions for distances between the outlet of the upstream nozzle and the inlet of the downstream nozzle of 35 mm (shown in FIG. 37D), 12 mm, and 4 mm, respectively. The same upstream nozzle was used as above and the downstream nozzle has an inlet inner diameter of 5 mm. For data points 208 where the distance is 35 mm, similar to data points 206, renal flow is actually negative, which would send blood flow in the renal veins in the wrong direction. In addition, the table below confirms the pressure loss of 22 mmHg is high. For data points 210 and 212, the renal flow is around or worse than baseline and the pressure loss is high at 14 mmHg.

| Configuration | Pressure loss [mmHg] |
| --- | --- |
| Nozzle and diffuser | 5 |
| Nozzle | 11 |

| Configuration | Pressure loss [mmHg] |
| --- | --- |
| 2 Nozzle same direction | 22 |
| 2 Nozzle opposite direction distance −35 mm | 22 |
| 2 Nozzle opposite direction distance −12 mm | 14 |
| 2 Nozzle opposite direction distance −4 mm | 14 |

Thus, Applicant has discovered that using a maximum distance between the outlet of the upstream component and the entry to the downstream component will improve flow rates in the branched vessel(s) with relatively low pressure loss. A distance too great will create a significant pressure loss that actually sends flow in the wrong direction in the renal vein(s). In addition, other structural characteristics of the downstream component improve renal flow with low pressure loss such as a greater inner diameter at the entry of the downstream component than the inner diameter at the outlet of the upstream component, a greater length of the diverging area of the downstream component than the length of the converging area of the upstream component, and/or a lesser average angle of divergence of the downstream component than the average angle of convergence of the upstream component.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method for modifying blood flow to treat heart failure, the method comprising:
    percutaneously delivering a flow modulator compressed in a delivery sheath into an inferior vena cava, the flow modulator comprising a frame having a coating;
    deploying a downstream diffuser of the flow modulator from the delivery sheath within the inferior vena cava downstream from a branch off to a renal vein, wherein the downstream diffuser comprises a cross-sectional flow area that diverges from an entry of the downstream diffuser in a downstream direction towards an exit of the downstream diffuser; and
    deploying an upstream nozzle of the flow modulator from the delivery sheath within the inferior vena cava upstream from the branch off to the renal vein such that uncoated portions of the frame, which are located around a circumference of the downstream diffuser where the downstream diffuser is diverging, define a gap positioned where the branch off to the renal vein intersects with the inferior vena cava,
    wherein blood flow passing through the upstream nozzle is accelerated towards the downstream diffuser to generate a low pressure region in a vicinity of the gap to draw and entrain additional blood into the flow modulator via the gap from the renal vein, thereby treating heart failure.

2. The method of claim 1, wherein the coating comprises polyurethane.

3. The method of claim 1, wherein the frame comprises nitinol.

4. The method of claim 1, wherein the upstream nozzle and the downstream diffuser are formed from the frame having the coating.

5. The method of claim 1, wherein the upstream nozzle and the downstream diffuser are formed from the frame which is a single frame.

6. The method of claim 1, wherein the upstream nozzle comprises a cross-sectional flow area that converges from an inlet of the upstream nozzle in a downstream direction towards an outlet of the upstream nozzle.

7. The method of claim 1, wherein deploying the downstream diffuser and the upstream nozzle comprises expanding the downstream diffuser and the upstream nozzle within the inferior vena cava.

8. The method of claim 1, wherein the flow modulator is configured for an acute treatment, the method further comprising: after the acute treatment, removing the flow modulator from the inferior vena cava.

9. The method of claim 1, wherein a cross-sectional flow area at an outlet of the upstream nozzle is less than a cross-sectional flow area at an entry of the downstream diffuser.

10. The method of claim 1, wherein the upstream nozzle and the downstream diffuser are configured to share a common, collinear flow axis with the inferior vena cava's flow axis.

11. The method of claim 1, wherein the upstream nozzle's average angle of convergence is greater than the downstream diffuser's average angle of divergence.

12. The method of claim 1, wherein the downstream diffuser's length is greater than the upstream nozzle's length.

13. The method of claim 1, wherein the gap's length is equal to a distance between an outlet of the upstream nozzle and an entry of the downstream diffuser.

14. The method of claim 13, wherein the distance between the outlet of the upstream nozzle and the entry of the downstream diffuser is less than 15 mm.

15. The method of claim 1, wherein drawing blood from the renal vein improves kidney functionality.

16. The method of claim 1, wherein the flow modulator modulates blood flow without any input from an external energy source.

17. The method of claim 1, wherein the flow modulator further comprises a retrieval portion extending in an upstream direction from an inlet of the upstream nozzle, the method further comprising:
coupling a retrieval device to the retrieval portion; and
pulling the retrieval portion via the retrieval device to compress the flow modulator into a collapsed delivery state.

18. The method of claim 17, wherein the retrieval portion comprises a cross-sectional area that converges from the inlet towards an upstream end of the retrieval portion.

19. The method of claim 18, wherein the upstream end of the retrieval portion comprises a hook.

* * * * *